(12) United States Patent
Nishio et al.

(10) Patent No.: US 11,879,150 B2
(45) Date of Patent: Jan. 23, 2024

(54) TREATMENT SELECTION METHOD AND BIOMARKER INDICATING SELECTION

(71) Applicants: YAKULT HONSHA CO., LTD., Tokyo (JP); KINKI UNIVERSITY, Osaka (JP)

(72) Inventors: Kazuto Nishio, Osaka (JP); Yoshihiko Fujita, Osaka (JP)

(73) Assignees: YAKULT HONSHA CO., LTD., Tokyo (JP); KINKI UNIVERSITY, Osaka (JP)

(*) Notice: Subject to any disclaimer, the term of this patent is extended or adjusted under 35 U.S.C. 154(b) by 678 days.

(21) Appl. No.: 15/762,834

(22) PCT Filed: Sep. 23, 2016

(86) PCT No.: PCT/JP2016/004327
§ 371 (c)(1),
(2) Date: Mar. 23, 2018

(87) PCT Pub. No.: WO2017/051542
PCT Pub. Date: Mar. 30, 2017

(65) Prior Publication Data
US 2018/0285521 A1    Oct. 4, 2018

(30) Foreign Application Priority Data
Sep. 24, 2015  (JP) ................ 2015-187300

(51) Int. Cl.
*C12Q 1/6827* (2018.01)
*G16B 30/00* (2019.01)
(Continued)

(52) U.S. Cl.
CPC .......... *C12Q 1/6827* (2013.01); *C12Q 1/68* (2013.01); *C12Q 1/6886* (2013.01); *G16B 30/00* (2019.02);
(Continued)

(58) Field of Classification Search
CPC ........ G16B 30/00; C12Q 1/68; C12Q 1/6886; C12Q 1/6827; C12Q 2600/106; C12Q 2600/156; G16H 50/20
See application file for complete search history.

(56) References Cited

U.S. PATENT DOCUMENTS

2006/0088871 A1* 4/2006 Finkelstein ............ G16H 50/30
435/6.14
2011/0105341 A1* 5/2011 Semizarov ....... G01N 33/57423
506/7
(Continued)

FOREIGN PATENT DOCUMENTS

CN    103710451 A    4/2014
CN    104762375 A    7/2015
(Continued)

OTHER PUBLICATIONS

Smith, David Hersi, et al. "Mechanisms of topoisomerase I (TOP1) gene copy number increase in a stage III colorectal cancer patient cohort." PloS one 8.4 (2013): e60613. (Year: 2013).*
(Continued)

*Primary Examiner* — Jesse P Frumkin
(74) *Attorney, Agent, or Firm* — Greeblum & Bernstein, P.L.C

(57) ABSTRACT

Treating colorectal cancer in a stage IV uses a systemic chemotherapy, either a FOLFOX regimen or a FOLFIRI regimen. However, a method of predicting which of the regimens is effective to an individual patient would be advantageous. Provided is a biomarker that indicates which of the regimens, the FOLFOX regimen or the FOLFIRI regimen, is advantageous to select for a patient having colorectal cancer. The biomarker is characterized by being a gain in the copy number of at least one region on human chromosomes among 7p15.3, 7q34, 8q24.1, 8q24.2, 8q24.1-q24.2, 9q34.3, 13q12.2, 13q14.11, 13q22.1, 13q32.2-q32.3,
(Continued)

13q34, 20q12, 20q13.13, 20q13.2, and 20q13.3. Using such a biomarker enables to determine which, the FOLFOX regimen or the FOLFIRI regimen, is more advantageously selected.

4 Claims, 23 Drawing Sheets

(51) Int. Cl.
    *C12Q 1/68*     (2018.01)
    *C12Q 1/6886*     (2018.01)
    *G16H 50/20*     (2018.01)

(52) U.S. Cl.
    CPC ....... *G16H 50/20* (2018.01); *C12Q 2600/106* (2013.01); *C12Q 2600/156* (2013.01)

(56) References Cited

U.S. PATENT DOCUMENTS

| | | | |
|---|---|---|---|
| 2011/0165577 A1* | 7/2011 | Brunner | G01N 33/57419 |
| | | | 435/6.12 |
| 2011/0262464 A1 | 10/2011 | Chin et al. | |
| 2012/0231020 A1 | 9/2012 | Corro et al. | |
| 2017/0283884 A1* | 10/2017 | Knudsen | A61K 31/15 |

FOREIGN PATENT DOCUMENTS

| | | |
|---|---|---|
| CN | 04878083 A | 9/2015 |
| JP | 2008-048689 | 3/2008 |
| JP | 2008-524986 | 7/2008 |
| JP | 2010-162029 | 7/2010 |
| JP | 2011-135838 | 7/2011 |
| JP | 2012504426 A | 2/2012 |
| JP | 2013503616 A | 2/2013 |
| JP | 2013507987 A | 3/2013 |
| WO | 2006/061216 | 6/2006 |
| WO | 2010/040124 | 4/2010 |
| WO | 2011/056489 | 5/2011 |

OTHER PUBLICATIONS

González-González, María, et al. "Association between the cytogenetic profile of tumor cells and response to preoperative radiochemotherapy in locally advanced rectal cancer." Medicine 93.26 (2014). (Year: 2014).*

Arcaroli, John J., et al. "ALDH+ tumor-initiating cells exhibiting gain in NOTCH1 gene copy number have enhanced regrowth sensitivity to a γ-secretase inhibitor and irinotecan in colorectal cancer." Molecular oncology 6.3 (2012): 370-381. (Year: 2012).*

Dionigi, Adriana, Carla Facco, Maria Grazia Tibiletti, Barbara Bernasconi, Cristina Riva, and Carlo Capella. "Ovarian metastases from colorectal carcinoma: Clinicopathologic profile, immunophenotype, and karyotype analysis." American journal of clinical pathology 114, No. 1 (2000): 111-122. (Year: 2000).*

Mohelnikova-Duchonova, Beatrice, Bohuslav Melichar, and Pavel Soucek. "FOLFOX/FOLFIRI pharmacogenetics: The call for a personalized approach in colorectal cancer therapy." World journal of gastroenterology: WJG 20, No. 30 (2014): 10316. (Year: 2014).*

Kim et al., "Pretreatment Selection of Regimen According to Genetic Analysis Improves the Efficacy of Chemotherapy in the First Line Treatment of Metastatic Colorectal Cancer", Journal of Surgical Oncology, vol. 109, No. 3, Mar. 2014, pp. 250-254, ISSN 0022-4790.

Miyaki et al., "Identification of a potent epigenetic biomarker for resistance to campothecin and poor outcome to irinotecan-based chemotherapy in colon cancer", International Journal of Oncology, vol. 40, No. 1, Jan. 2012, pp. 217-226, ISSN 1019-6439.

Mohelnikova-Duchonova et al., "FOLFOX/FOLFIRI pharmacogenetics: the call for a personalized approach in colorectal cancer therapy", World Journal of Gastroenterology, vol. 20, No. 30, Aug. 14, 2014, pp. 10316-10330, ISSN 1007-9327.

Yuan et al., "Identification of the Biomarkers for the Prediction of Efficacy in First-Line Chemotherapy of Metastatic Colorectal Cancer Patients using SELDI-TOF-MS and Artifical Neural Networks", Hepatogastroenterology, vol. 59, No. 120, Nov. 2012, pp. 2461-2465, ISSN 0172-6390.

Official Communication issued in International Bureau of WIPO Patent Application No. PCT/JP2016/004327, dated Dec. 27, 2016.

Josien C. Hmn et al: "Genomic landscape of metastatic colorectal cancer", Nature Communications, vol. 5, No. 1, Nov. 14, 2014 (Nov. 14, 2014), XP055566002.

George Poulogiannis et al: "Prognostic relevance of DNA copy number changes in colorectal cancer", The Journal of Pathology, vol. 220, No. 3, Feb. 1, 2010 Feb. 1, 2010, pp. 338-347, XP055566105.

Leticia G. Leon et al: "DNA Copy Number Profiles Correlate with Outcome in Colorectal Cancer Patients Treated with Fluoropyrimidine/Antifolate-based Regimens", Current Drug Metabolism, Dec. 1, 2011 (Dec. 1, 2011), pp. 956-965, XP055565934.

C. Postma et al: "DNA copy number profiles of primary tumors as predictors of response to chemotherapy in advanced colorectal cancer", Annals of Oncology., vol. 20, No. 6, Jan. 15, 2009 (Jan. 15, 2009) pp. 1048-1056, XP055377256.

H Wang et al: "Somatic gene copy number alterations in colorectal cancer: new quest for cancer drivers and biomarkers", Oncogene, vol. 35, No. 16, Aug. 10, 2015 Aug. 10, 2015 , pp. 2011-2019, XP055377249.

* cited by examiner

| Aberration | Chr | Cytoband | Start | Stop | #Probes | Amplification | Deletion | pval | Gene Names |
|---|---|---|---|---|---|---|---|---|---|
| 221 | | | | | | | | | |
| 1 | chr1 | q36.21 | 13885132 | 14990172 | 53 | 0 | -0.54065 | 8.35E-14 | PRDM2, KIAA1026 |
| 2 | chr1 | p34.3 | 36293439 | 38220157 | 125 | 1.561294 | 0 | 0 | EIF2C3, TEKT2, ADPRHL2, COL8A2, TRAPPC3, MAP7D1, THRAP3, C1orf113, FAM176B, STK40, LSM10, C1orf10 |
| 3 | chr1 | p34.3 | 36328610 | 37826666 | 100 | 1.621386 | 0 | 1.65E-34 | ADPRHL2, COL8A2, TRAPPC3, MAP7D1, THRAP3, C1orf113, FAM176B, STK40, LSM10, C1orf102, MRPS15, CSF |
| 4 | chr1 | p34.3 - p3 | 38220217 | 42516636 | 301 | 1.348407 | 0 | 0 | SF3A3, FHL3, UTP11L, POU3F1, RRAGC, MYCBP, GJA9, RHBDL2, AKIRIN1, NDUFS5, MACF1, KIAA0754, BMP8A |
| 5 | chr1 | p34.2 - p3 | 42516755 | 49228814 | 503 | 1.206663 | 0 | 0 | FOXJ3, RIMKLA, ZMYND12, PPCS, LOC728621, FPIH, YBX1, CLDN19, LEPRE1, C1orf50, CCDC23, ERMAP, ZNF6 |
| 6 | chr1 | p33 | 46873284 | 48649723 | 119 | 0.876439 | 0 | 1.55E-68 | ATPAF1, C1orf223, KIAA0494, CYP4B1, CYP4A11, CYP4Z1, CYP4X1, CYP4Z2P, PDZK1IP1, TAL1, STIL |
| 7 | chr1 | p21.3 | 97988607 | 97987795 | 5 | 0 | -1.19097 | 8.77E-19 | DPYD |
| 8 | chr1 | q25.2 | 1.78E+08 | 1.78E+08 | 11 | 0.492259 | 0 | 1.55E-10 | QSOX1, FLJ23867, LHX4 |
| 9 | chr1 | q24.1 | 210278980 | 220025597 | 35 | 0 | -0.31493 | 7.00E-13 | APOB |
| 10 | chr2 | p11.2 | 85346737 | 86362427 | 80 | 0.332111 | 0 | 6.90E-30 | TCF7L1, TGOLN2, RETSAT, ELMOD3, CAPG, SH2D6, MAT2A, GGCX, VAMP8, VAMP5, RNF181, TMEM150, C2orf6 |
| 11 | chr2 | q14.2 | 1.21E+08 | 1.22E+08 | 38 | 0.307284 | 0 | 2.99E-13 | GLI2, TFCP2L1, CLASP1 |
| 12 | chr3 | q26.1 | 1.64E+08 | 1.64E+08 | 6 | 0 | -3.63802 | 3.01E-100 | |
| 13 | chr4 | p15.1 - q1 | 28114310 | 35888708 | 225 | 0 | -0.42984 | 1.11E-99 | PCDH7, ARAP2 |
| 14 | chr4 | p12 - q13 | 58164089 | 66922262 | 294 | 0 | -0.37319 | 1.30E-23 | LPHN3, SRD5A2L2, EPHA5 |
| 15 | chr4 | q13.2 | 69075140 | 69108871 | 4 | 0 | -3.86693 | 8.51E-41 | UGT2B17 |
| 16 | chr5 | p15.33 | 216401 | 1543921 | 94 | 0.376227 | 0 | 4.74E-44 | PLEKHG4B, LOC389257, CCDC127, SDHA, PDCD6, AHRR, C5orf55, EXOC3, LOC25845, SLC9A3, CEP72, IPPP |
| 17 | chr5 | q12.1 - q1 | 59031890 | 94996499 | 1912 | 0 | -0.61112 | 0 | PDE4D, PART1, DEPDC1B, ELOVL7, ERCC8, NDUFAF2, C5orf43, ZSWIM6, FLJ37543, KIF2A, DIMT1L, IPO11, LRR |
| 18 | chr6 | p25.3 - p2 | 99130 | 9490261 | 580 | 0.463892 | 0 | 0 | DUSP22, IRF4, EXOC2, HUS1B, LOC285768, FOXQ1, FOXF2, FOXC1, GMDS, C6orf195, MYLK4, WRNIP1, SERPIN |
| 19 | chr6 | p24.3 - p2 | 10492784 | 57754769 | 3166 | 0.442834 | 0 | 0 | TFAP2A, C6orf218, GCNT2, C6orf52, PAK1IP1, TMEM14B, MAK, GCM2, SYCP2L, ELOVL2, LOC22171 |
| 20 | chr6 | p21.33 | 29962849 | 30034659 | 5 | 0 | -3.96922 | 2.40E-82 | HLA-H, HCG2P7, HCG4P6 |
| 21 | chr6 | p21.33 - p | 30178750 | 44385884 | 1114 | 0.594174 | 0 | 2.20E-80 | TRIM31, TRIM40, TRIM10, TRIM15, TRIM26, FLJ45422, HCG18, TRIM39, RPP21, HLA-E, GNL1, PRR3, ABCF1, PP |
| 22 | chr6 | p21.32 | 32558677 | 32650731 | 5 | 0 | -0.74676 | 2.27E-19 | HLA-DRB5, HLA-DRB6 |
| 23 | chr6 | p21.2 | 37916898 | 40524289 | 185 | 0.410338 | 0 | 7.60E-22 | ZFAND3, BTBD9, GLO1, DNAH8, TRIM38, GLP1R, C6orf64, KCNK5, KCNK17, KIF6, DAAM2, MOCS1, TDRG1, LRF |
| 24 | chr6 | p21.1 | 44856727 | 57754769 | 802 | 0.312244 | 0 | 1.29E-46 | SUPT3H, RUNX2, CLIC5, ENPP4, RCAN2, CYP39A1, SLC25A27, TDRD6, PLA2G7, MEP1A, GPR116, GPR1 |
| 25 | chr6 | q21 | 1.06E+08 | 1.13E+08 | 477 | 0.450519 | 0 | 3.34E-45 | PREP, PRDM1, ATG5, AIM1, RTN4IP1, QRSL1, LOC553137, C6orf203, BEND3, PDSS2, SOBP, SCML4, SEC63, OS |
| 26 | chr7 | p22.3 - p2 | 128408 | 6337468 | 449 | 0.688598 | 0 | 0 | FAM20C, PDGFA, PRKAR1B, HEATR2, HEATR2, UNC84A, C7orf20, ADAP1, COX19, CYP2W1, C7orf50, GPR146, GPER, ZFA |
| 27 | chr7 | p22.3 - p2 | 1.78E+08 | 1.78E+08 | 1882 | 0.447941 | 0 | 1.31E-95 | FAM20C, PDGFA, PRKAR1B, HEATR2, HEATR2, UNC84A, C7orf20, ADAP1, COX19, CYP2W1, C7orf50, GPR146, GPER, ZFA |
| 28 | chr7 | p15.3 - p1 | 21750644 | 53503164 | 125 | 0.712234 | 0 | 3.67E-35 | DNAH11, CDCA7L, RAPGEF5, IL6, TOMM7, SNORD93, FAM126A, KLHL7, NUPL2, GPNMB, C7orf30, IGF2BP3, RP |
| 29 | chr7 | p13 | 43788129 | 45228079 | 125 | 0.462584 | 0 | 0 | BLVRA, MRPS24, URG4, UBE2D4, POLR2J4, SPDYE1, RASA4P, FLJ35390, DBNL, PGAM2, POLM, AEBP1, PGLD2 |
| 30 | chr7 | q11.21 | 54403181 | 57548600 | 132 | 0.462584 | 0 | 0 | VSTM2A, SEC61G, EGFR, LANCL2, ECOP, LOC442308, FKBP9L, SEPT14, ZNF713, MRPS17, GBAS, PSPH, CCT6 |
| 31 | chr7 | q11.21 - q | 62098100 | 77810237 | 775 | 0.534846 | 0 | 0 | LOC643955, ZNF735, ZNF679, ZNF680, ZNF107, ZNF138, LOC168474, ZNF273, ZNF117, INTS4L1, ZNF92, INTS4 |
| 32 | chr7 | q11.22 - q | 71029344 | 75962676 | 246 | 0.724528 | 0 | 3.71E-86 | CALN1, TYW1B, SBDSP, SPDYE7P, POM121, NSUN5C, TRIM74, STAG3L3, PMS2L2, SPDYE8P, LOC100093631, |

*FIG. 1B*

Fig. 9
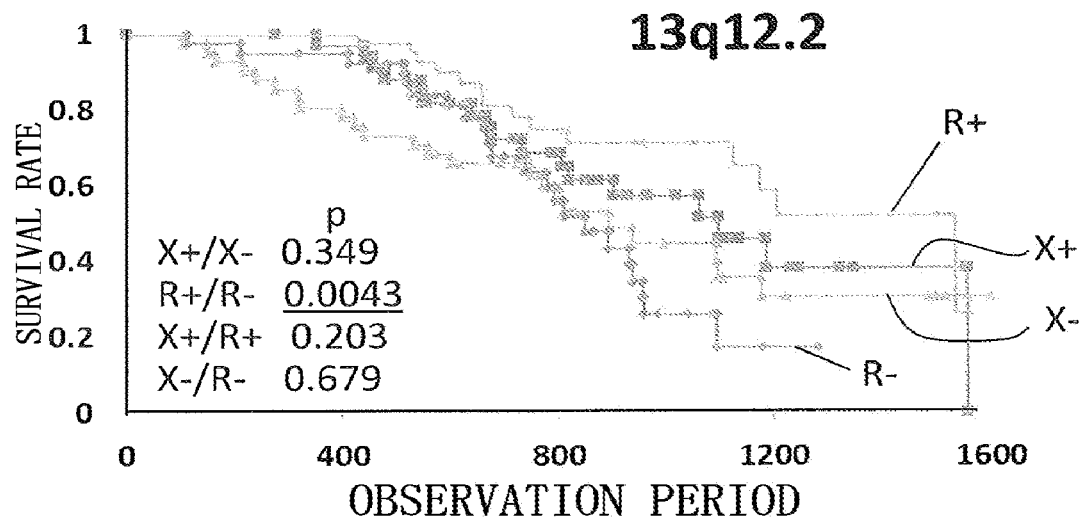
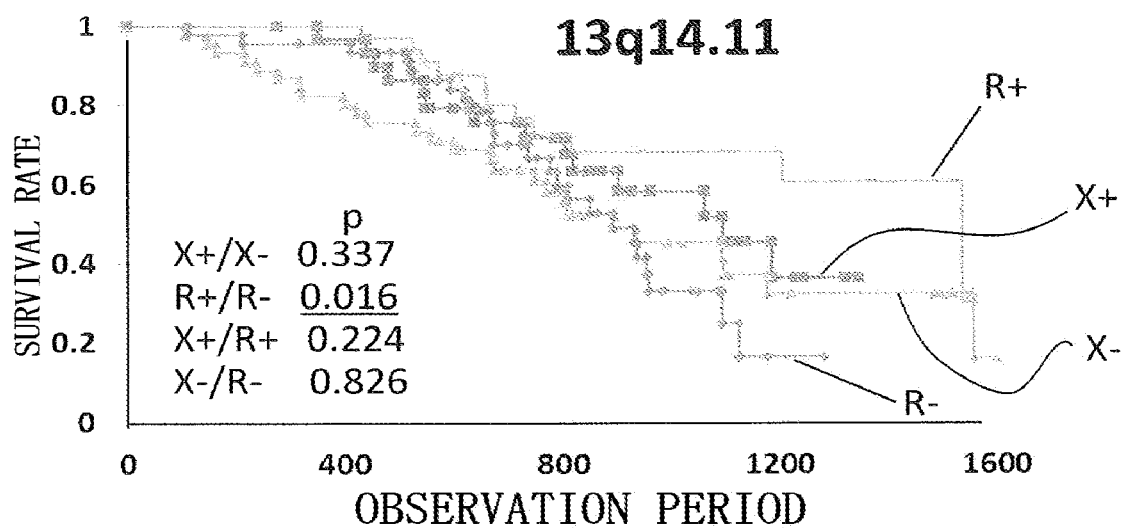

Fig. 10
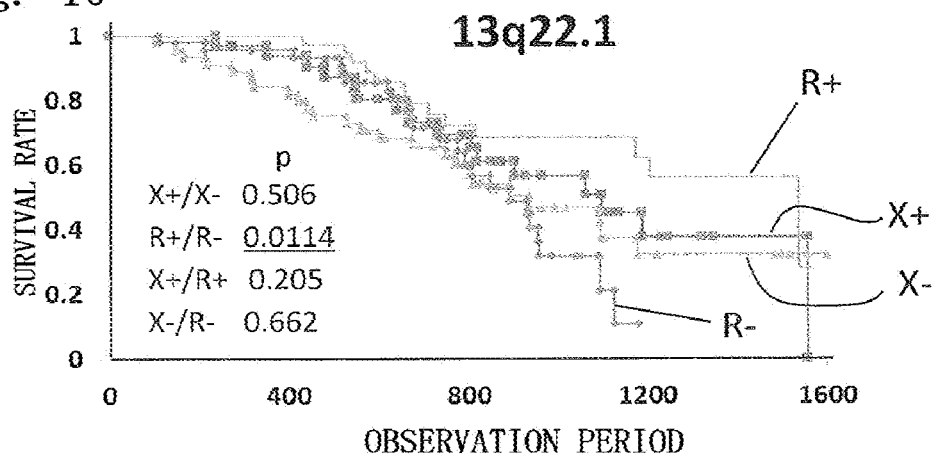
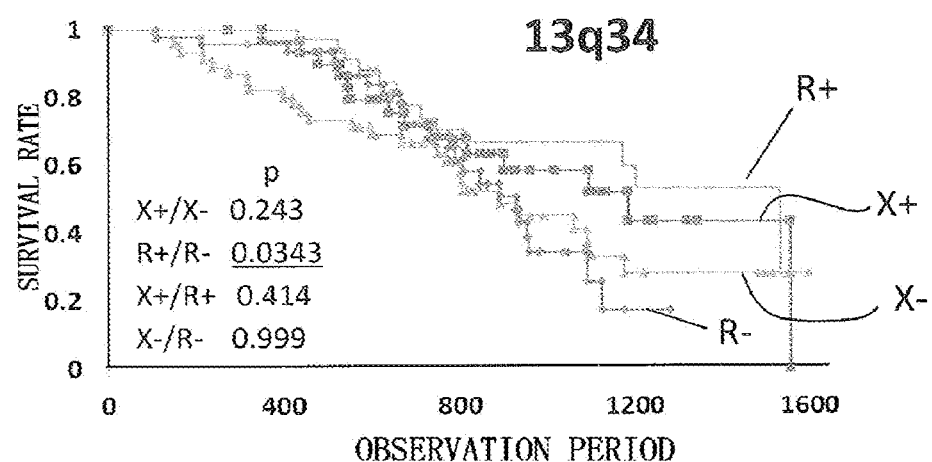
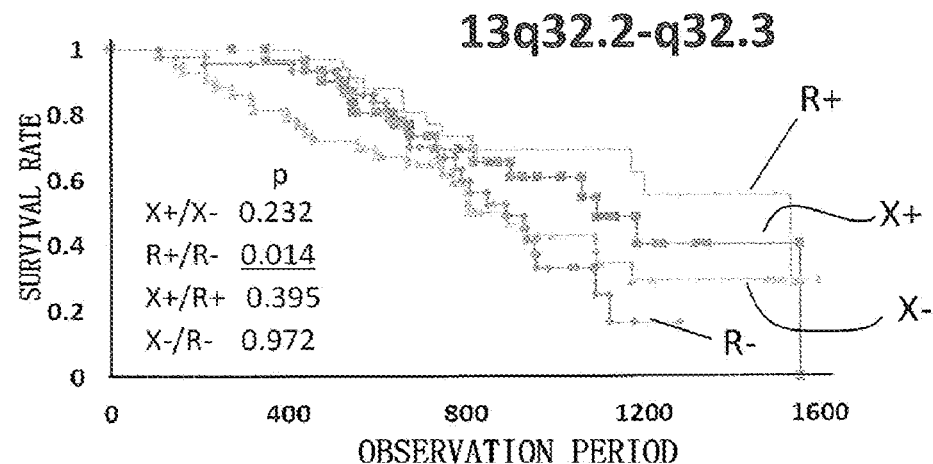

Fig. 11
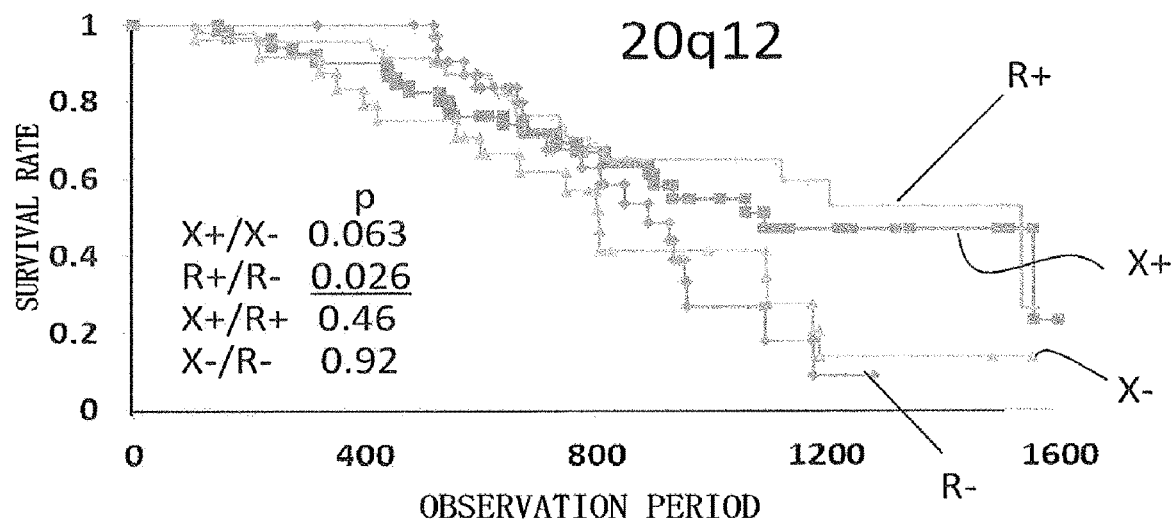
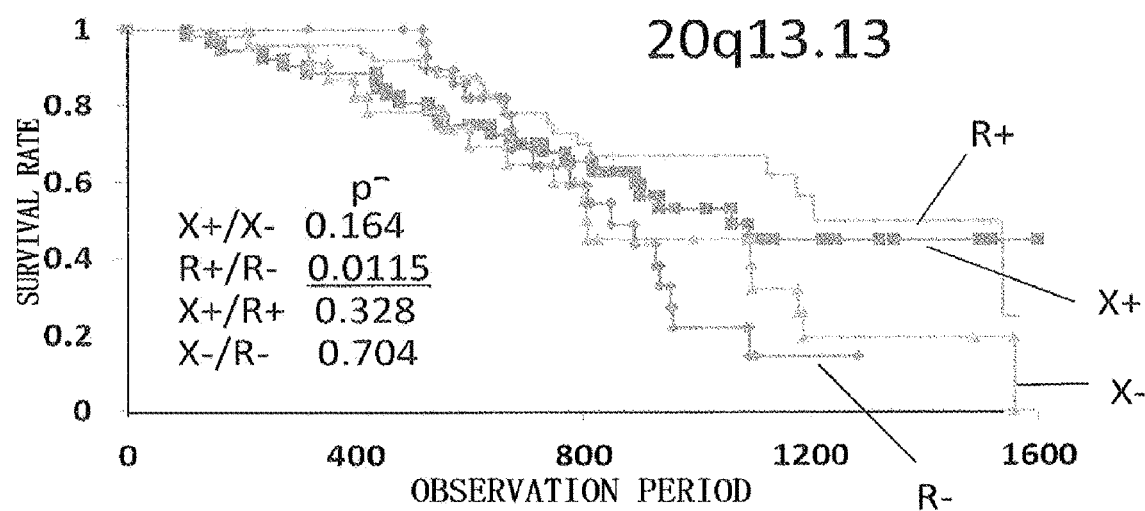

Fig. 12
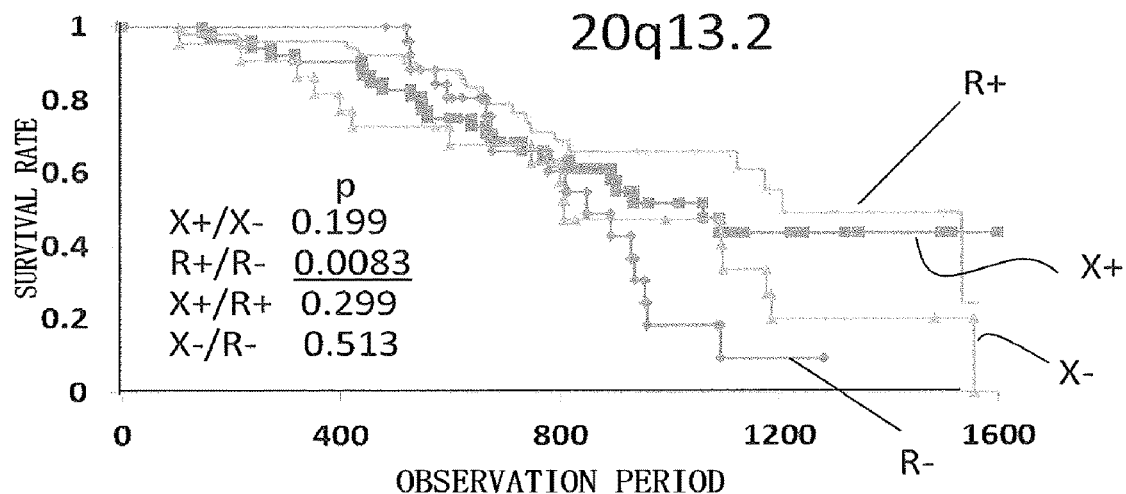
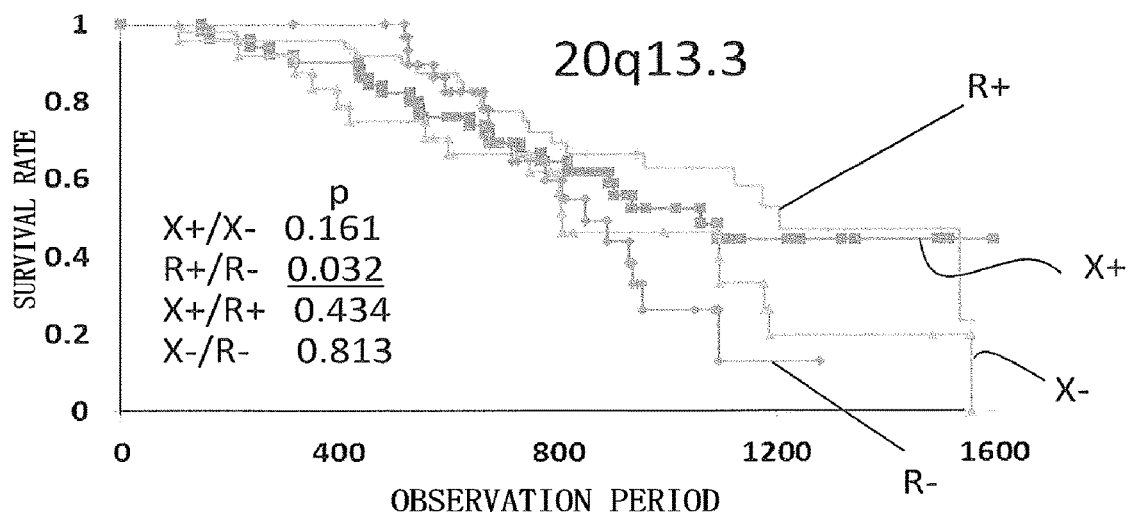

Fig. 13

| Chr | Sub-region | total (154) | | | ox-arm (75) | | | iri-arm (79) | | | CNG (+) | | | CNG (-) | | |
|---|---|---|---|---|---|---|---|---|---|---|---|---|---|---|---|---|
| | | n | PFS | OS | n | PFS | OS | n | PFS | OS | n | PFS | OS | n | PFS | OS |
| 7 | p22.3 | 64 | 0.923 | 0.307 | 29 | 0.597 | 0.066 | 35 | 0.637 | 0.625 | 29:35 | 0.744 | 0.457 | 46:44 | 0.070 | 0.062 |
| 7 | 22.2~p22. | 67 | 0.987 | 0.415 | 31 | 0.649 | 0.129 | 36 | 0.639 | 0.667 | 31:36 | 0.628 | 0.649 | 44:43 | 0.091 | 0.087 |
| 7 | p21 | 54 | 0.571 | 0.375 | 26 | 0.870 | 0.235 | 28 | 0.611 | 0.943 | 25:28 | 0.412 | 0.849 | 49:51 | 0.141 | 0.187 |
| 7 | p15.3 | 54 | 0.997 | 0.197 | 26 | 0.547 | 0.081 | 28 | 0.611 | 0.943 | 26:28 | 0.821 | 0.604 | 49:51 | 0.059 | 0.112 |
| 7 | p15.2 | 64 | 0.771 | 0.501 | 32 | 0.707 | 0.523 | 32 | 0.915 | 0.740 | 32:32 | 0.263 | 0.766 | 43:47 | 0.249 | 0.354 |
| 7 | p15.1 | 55 | 0.894 | 0.214 | 27 | 0.671 | 0.090 | 28 | 0.611 | 0.942 | 27:28 | 0.731 | 0.657 | 48:51 | 0.070 | 0.111 |
| 7 | p14 | 56 | 0.863 | 0.265 | 28 | 0.698 | 0.125 | 28 | 0.611 | 0.942 | 28:28 | 0.721 | 0.730 | 47:51 | 0.074 | 0.130 |
| 7 | p13 | 57 | 0.977 | 0.249 | 27 | 0.665 | 0.076 | 30 | 0.670 | 0.877 | 27:30 | 0.684 | 0.546 | 48:49 | 0.077 | 0.088 |
| 7 | p12 | 54 | 0.867 | 0.092 | 26 | 0.527 | 0.051 | 28 | 0.759 | 0.665 | 26:28 | 0.712 | 0.670 | 49:51 | 0.068 | 0.125 |
| 7 | p11.2 | 53 | 0.742 | 0.109 | 25 | 0.395 | 0.067 | 28 | 0.759 | 0.665 | 25:28 | 0.818 | 0.696 | 50:51 | 0.055 | 0.196 |
| 7 | q11.21 | 39 | 0.234 | 0.005 | 18 | 0.656 | 0.103 | 21 | 0.254 | 0.014 | 18:21 | 0.220 | 0.487 | 57:58 | 0.266 | 0.607 |
| 7 | q11.22 | 42 | 0.264 | 0.011 | 20 | 0.403 | 0.062 | 22 | 0.467 | 0.069 | 20:22 | 0.488 | 0.905 | 55:57 | 0.149 | 0.419 |
| 7 | q11.23 | 44 | 0.235 | 0.016 | 20 | 0.497 | 0.100 | 23 | 0.344 | 0.065 | 21:23 | 0.385 | 0.773 | 55:56 | 0.207 | 0.487 |
| 7 | q21.1 | 37 | 0.277 | 0.007 | 18 | 0.529 | 0.194 | 19 | 0.351 | 0.010 | 18:19 | 0.315 | 0.301 | 57:60 | 0.206 | 0.806 |
| 7 | q21.2 | 33 | 0.585 | 0.012 | 16 | 0.923 | 0.261 | 17 | 0.352 | 0.012 | 16:17 | 0.107 | 0.266 | 59:62 | 0.328 | 0.810 |
| 7 | q21.3 | 41 | 0.406 | 0.029 | 21 | 0.497 | 0.100 | 20 | 0.563 | 0.124 | 21:20 | 0.497 | 0.846 | 54:59 | 0.134 | 0.391 |
| 7 | q22 | 46 | 0.241 | 0.020 | 23 | 0.353 | 0.096 | 23 | 0.471 | 0.085 | 23:23 | 0.493 | 0.761 | 52:56 | 0.173 | 0.441 |
| 7 | q31.1 | 33 | 0.186 | 0.006 | 15 | 0.368 | 0.216 | 18 | 0.356 | 0.007 | 15:18 | 0.470 | 0.255 | 60:61 | 0.174 | 0.845 |
| 7 | q31.2 | 34 | 0.419 | 0.026 | 15 | 0.938 | 0.510 | 19 | 0.341 | 0.014 | 15:19 | 0.120 | 0.177 | 60:60 | 0.344 | 0.962 |
| 7 | q31.3 | 33 | 0.254 | 0.005 | 16 | 0.369 | 0.092 | 17 | 0.430 | 0.021 | 16:17 | 0.499 | 0.535 | 59:62 | 0.142 | 0.599 |
| 7 | q32 | 44 | 0.831 | 0.098 | 23 | 0.673 | 0.776 | 21 | 0.508 | 0.034 | 23:21 | 0.122 | 0.148 | 52:58 | 0.397 | 0.975 |
| 7 | q33 | 36 | 0.465 | 0.013 | 18 | 0.656 | 0.103 | 18 | 0.515 | 0.048 | 18:18 | 0.370 | 0.618 | 57:61 | 0.179 | 0.467 |
| 7 | q34 | 39 | 0.316 | 0.005 | 20 | 0.403 | 0.062 | 19 | 0.516 | 0.030 | 20:19 | 0.478 | 0.657 | 55:60 | 0.130 | 0.471 |
| 7 | q35 | 32 | 0.348 | 0.020 | 16 | 0.523 | 0.209 | 16 | 0.426 | 0.034 | 16:16 | 0.448 | 0.388 | 59:63 | 0.156 | 0.642 |
| 7 | q36 | 40 | 0.443 | 0.023 | 18 | 0.996 | 0.252 | 22 | 0.411 | 0.036 | 18:22 | 0.232 | 0.458 | 57:57 | 0.279 | 0.688 |

Fig. 14

| Chr | Sub-region | total (154) | | | ox-arm (75) | | | iri-arm (79) | | | CNG (+) | | | CNG (−) | | |
|---|---|---|---|---|---|---|---|---|---|---|---|---|---|---|---|---|
| | | n | PFS | OS | n | PFS | OS | n | PFS | OS | n | PFS | OS | n | PFS | OS |
| 8 | q11.1 | 30 | 0.385 | 0.098 | 15 | 0.491 | 0.347 | 15 | 0.438 | 0.164 | 15:15 | 0.597 | 0.472 | 60:64 | 0.113 | 0.454 |
| 8 | q11.21 | 35 | 0.579 | 0.179 | 18 | 0.848 | 0.712 | 17 | 0.431 | 0.119 | 18:17 | 0.374 | 0.223 | 57:62 | 0.180 | 0.655 |
| 8 | q11.22 | 33 | 0.436 | 0.112 | 16 | 0.643 | 0.506 | 17 | 0.431 | 0.119 | 16:17 | 0.456 | 0.360 | 59:62 | 0.148 | 0.587 |
| 8 | q11.23 | 33 | 0.436 | 0.112 | 16 | 0.643 | 0.506 | 17 | 0.431 | 0.119 | 16:17 | 0.456 | 0.360 | 59:62 | 0.148 | 0.587 |
| 8 | q12 | 42 | 0.617 | 0.518 | 23 | 0.990 | 0.604 | 19 | 0.307 | 0.122 | 23:19 | 0.210 | 0.068 | 52:60 | 0.278 | 0.957 |
| 8 | q13 | 41 | 0.947 | 0.614 | 22 | 0.913 | 0.678 | 19 | 0.628 | 0.227 | 22:19 | 0.349 | 0.141 | 53:60 | 0.204 | 0.840 |
| 8 | q21.1 | 43 | 0.963 | 0.569 | 23 | 0.706 | 0.477 | 20 | 0.561 | 0.114 | 23:20 | 0.250 | 0.074 | 52:59 | 0.260 | 0.942 |
| 8 | q21.2 | 43 | 0.930 | 0.440 | 23 | 0.706 | 0.477 | 20 | 0.588 | 0.061 | 23:20 | 0.271 | 0.046 | 52:59 | 0.248 | 0.867 |
| 8 | q21.3 | 43 | 0.946 | 0.519 | 24 | 0.555 | 0.399 | 19 | 0.419 | 0.062 | 24:19 | 0.163 | 0.037 | 51:60 | 0.338 | 0.820 |
| 8 | q22.1 | 49 | 0.544 | 0.792 | 26 | 0.479 | 0.293 | 23 | 0.901 | 0.130 | 26:23 | 0.247 | 0.045 | 49:56 | 0.285 | 0.798 |
| 8 | q22.2 | 50 | 0.380 | 0.788 | 29 | 0.228 | 0.135 | 21 | 0.704 | 0.193 | 29:21 | 0.145 | 0.036 | 46:58 | 0.452 | 0.697 |
| 8 | q22.3 | 52 | 0.344 | 0.790 | 29 | 0.228 | 0.135 | 23 | 0.858 | 0.214 | 29:23 | 0.149 | 0.040 | 46:56 | 0.428 | 0.691 |
| 8 | q23 | 51 | 0.297 | 0.655 | 30 | 0.152 | 0.079 | 21 | 0.694 | 0.186 | 30:21 | 0.116 | 0.026 | 45:58 | 0.523 | 0.600 |
| 8 | q24.1 | 62 | 0.316 | 0.915 | 32 | 0.060 | 0.026 | 30 | 0.717 | 0.037 | 32:30 | 0.037 | 0.004 | 43:49 | 0.787 | 0.233 |
| 8 | q24.2 | 66 | 0.307 | 0.689 | 35 | 0.091 | 0.015 | 31 | 0.783 | 0.045 | 35:31 | 0.053 | 0.004 | 40:48 | 0.801 | 0.200 |
| 8 | q24.3 | 61 | 0.860 | 0.765 | 33 | 0.249 | 0.120 | 28 | 0.357 | 0.039 | 33:28 | 0.068 | 0.018 | 42:51 | 0.625 | 0.360 |

Fig. 15

| Chr | Sub-region | total (154) | | | ox-arm (75) | | | iri-arm (79) | | | CNG (+) | | | CNG (-) | | |
|---|---|---|---|---|---|---|---|---|---|---|---|---|---|---|---|---|
| | | n | PFS | OS | n | PFS | OS | n | PFS | OS | n | PFS | OS | n | PFS | OS |
| 13 | q12.1 | 74 | 0.353 | 0.050 | 34 | 0.447 | 0.225 | 40 | 0.772 | 0.112 | 34:40 | 0.275 | 0.474 | 41:49 | 0.258 | 0.715 |
| 13 | q12.3 | 74 | 0.353 | 0.050 | 34 | 0.447 | 0.225 | 40 | 0.772 | 0.112 | 34:40 | 0.275 | 0.474 | 41:39 | 0.258 | 0.715 |
| 13 | q13 | 69 | 0.310 | 0.024 | 32 | 0.377 | 0.201 | 37 | 0.765 | 0.047 | 32:37 | 0.340 | 0.404 | 43:42 | 0.209 | 0.810 |
| 13 | q14.1 | 65 | 0.196 | 0.016 | 29 | 0.232 | 0.100 | 36 | 0.755 | 0.070 | 29:36 | 0.496 | 0.673 | 46:43 | 0.162 | 0.602 |
| 13 | q14.2 | 65 | 0.207 | 0.022 | 29 | 0.232 | 0.100 | 36 | 0.792 | 0.108 | 29:36 | 0.515 | 0.707 | 46:43 | 0.157 | 0.550 |
| 13 | q14.3 | 65 | 0.171 | 0.013 | 30 | 0.207 | 0.082 | 35 | 0.670 | 0.071 | 30:35 | 0.433 | 0.636 | 45:44 | 0.175 | 0.528 |
| 13 | q21.1 | 59 | 0.290 | 0.029 | 27 | 0.274 | 0.116 | 35 | 0.900 | 0.127 | 27:35 | 0.444 | 0.712 | 48:44 | 0.165 | 0.513 |
| 13 | q21.2 | 61 | 0.325 | 0.015 | 27 | 0.324 | 0.097 | 34 | 0.836 | 0.078 | 27:34 | 0.273 | 0.700 | 48:45 | 0.196 | 0.571 |
| 13 | q21.3 | 64 | 0.307 | 0.027 | 29 | 0.409 | 0.177 | 35 | 0.670 | 0.071 | 29:35 | 0.169 | 0.519 | 46:44 | 0.271 | 0.686 |
| 13 | q31 | 63 | 0.155 | 0.008 | 29 | 0.136 | 0.070 | 34 | 0.728 | 0.048 | 29:34 | 0.575 | 0.627 | 46:45 | 0.124 | 0.569 |
| 13 | q33 | 64 | 0.271 | 0.078 | 30 | 0.117 | 0.299 | 34 | 0.917 | 0.127 | 30:34 | 0.696 | 0.454 | 45:45 | 0.083 | 0.680 |
| 20 | p13 | 44 | 0.550 | 0.072 | 22 | 0.435 | 0.171 | 22 | 0.997 | 0.216 | 22:22 | 0.565 | 0.776 | 53:57 | 0.147 | 0.353 |
| 20 | p12 | 50 | 0.430 | 0.046 | 23 | 0.329 | 0.046 | 27 | 0.948 | 0.441 | 23:27 | 0.607 | 0.648 | 52:52 | 0.119 | 0.182 |
| 20 | p11.2 | 64 | 0.533 | 0.003 | 31 | 0.662 | 0.017 | 33 | 0.757 | 0.056 | 31:33 | 0.284 | 0.928 | 44:46 | 0.272 | 0.251 |
| 20 | p11.1 | 65 | 0.679 | 0.008 | 29 | 0.670 | 0.058 | 36 | 0.555 | 0.062 | 29:36 | 0.142 | 0.777 | 46:43 | 0.497 | 0.400 |
| 20 | q11.2 | 100 | 0.572 | 0.042 | 51 | 0.878 | 0.222 | 49 | 0.683 | 0.071 | 51:49 | 0.129 | 0.410 | 24:30 | 0.550 | 0.591 |
| 20 | q13.1 | 104 | 0.836 | 0.008 | 52 | 0.618 | 0.074 | 52 | 0.770 | 0.042 | 52:52 | 0.207 | 0.494 | 23:27 | 0.370 | 0.482 |

FIG. 19
7p15.3 vs 8q24.1
CNG (+, +)  CNG(+, −)
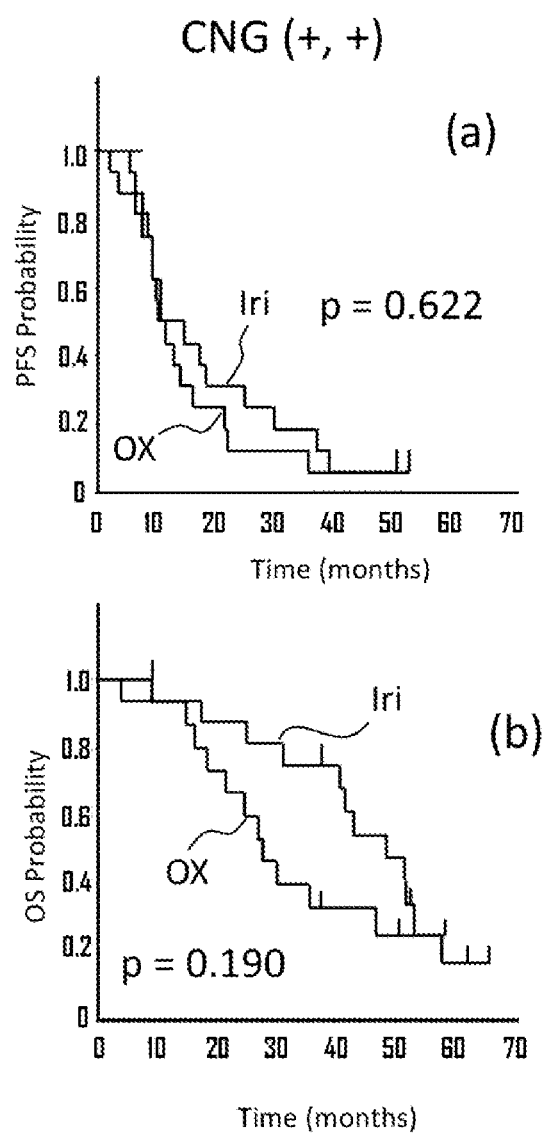
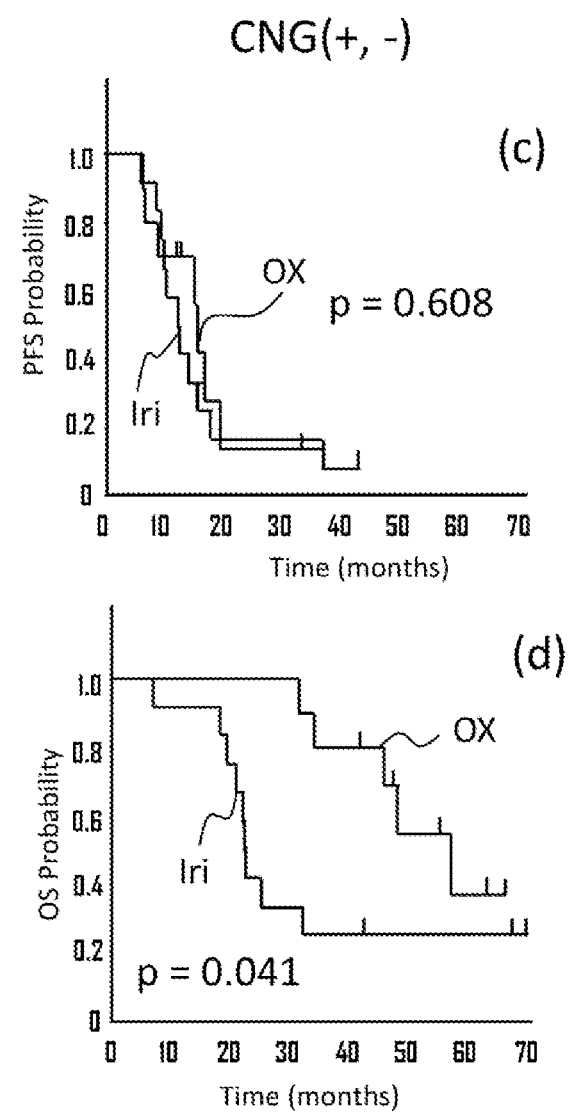
N = 32  N = 22

FIG. 20
7p15.3 vs 8q24.1
CNG (-, +)　　　　　　　　　　　CNG(-, -)
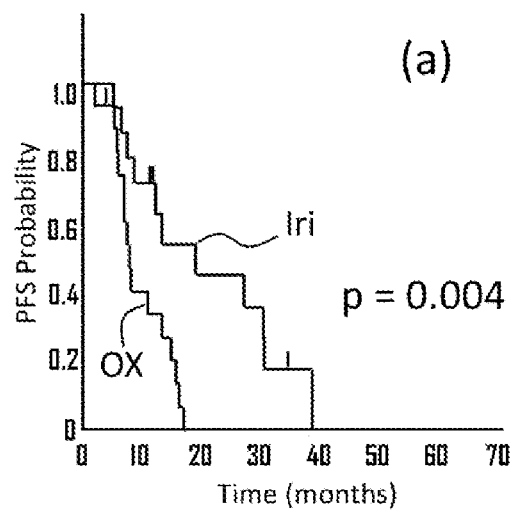
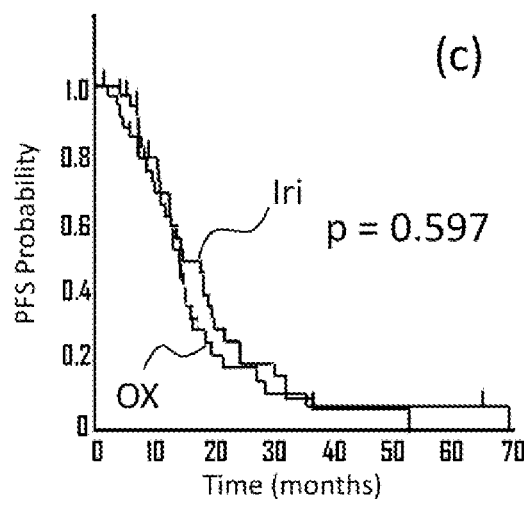
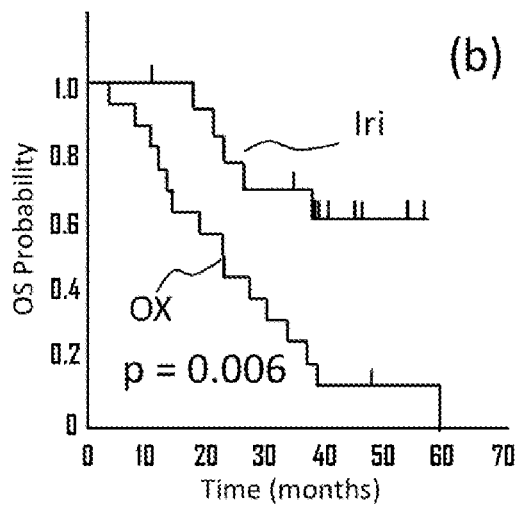
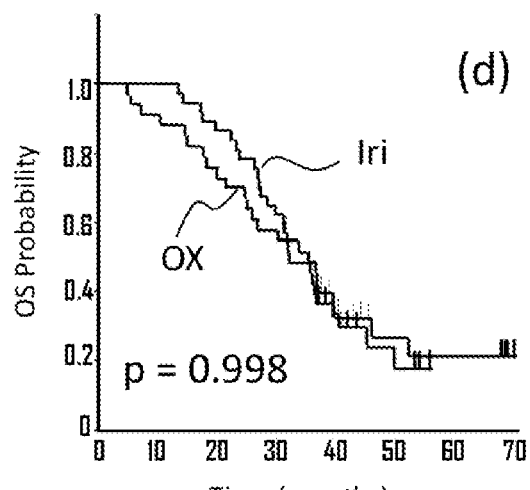
N = 30　　　　　　　　　　　　　N = 70

Fig. 21

| Chr | Sub-region | total (154) | | | ox-arm (75) | | | iri-arm (79) | | |
|---|---|---|---|---|---|---|---|---|---|---|
| | | n | PFS | OS | n | PFS | OS | n | PFS | OS |
| 1 | q21.1-q21.2 | 26 | 0.956 | 0.428 | 11 | 0.879 | 0.965 | 15 | 0.896 | 0.311 |
| 1 | q32.7 | 25 | 0.868 | 0.560 | 12 | 0.796 | 0.916 | 13 | 0.945 | 0.369 |
| 1 | q42.12 | 26 | 0.448 | 0.589 | 12 | 0.962 | 0.887 | 14 | 0.195 | 0.390 |
| 1 | q42.3 | 32 | 0.144 | 0.731 | 16 | 0.231 | 0.472 | 16 | 0.293 | 0.243 |
| 3 | q29 | 37 | 0.919 | 0.767 | 15 | 0.935 | 0.234 | 22 | 0.716 | 0.101 |
| 5 | p15.33 | 34 | 0.460 | 0.661 | 19 | 0.403 | 0.418 | 15 | 0.958 | 0.862 |
| 6 | p21.1 | 22 | 0.404 | 0.236 | 11 | 0.399 | 0.593 | 11 | 0.742 | 0.225 |
| 9 | p13.3-p13.2 | 15 | 0.467 | 0.610 | 8 | 0.724 | 0.090 | 7 | 0.162 | 0.144 |
| 9 | q34.3 | 17 | 0.555 | 0.817 | 9 | 0.110 | 0.094 | 8 | 0.149 | 0.083 |
| 11 | p15.5 | 19 | 0.500 | 0.283 | 13 | 0.553 | 0.465 | 6 | 0.630 | 0.293 |
| 12 | p13.31 | 22 | 0.166 | 0.773 | 12 | 0.399 | 0.687 | 10 | 0.297 | 0.954 |
| 16 | p11.2 | 26 | 0.293 | 0.275 | 10 | 0.834 | 0.536 | 16 | 0.246 | 0.363 |
| 16 | p12.1 | 28 | 0.708 | 0.476 | 13 | 0.390 | 0.782 | 15 | 0.571 | 0.413 |
| 16 | p12.3 | 27 | 0.736 | 0.440 | 13 | 0.390 | 0.782 | 14 | 0.545 | 0.352 |
| 16 | p13.2 | 25 | 0.929 | 0.558 | 13 | 0.390 | 0.782 | 12 | 0.372 | 0.469 |
| 16 | p13.3 | 23 | 0.824 | 0.888 | 12 | 0.927 | 0.831 | 11 | 0.544 | 0.905 |
| 16 | q21-q22.1 | 19 | 0.472 | 0.516 | 8 | 0.824 | 0.886 | 11 | 0.589 | 0.432 |
| 17 | q21.2 | 17 | 0.462 | 0.933 | 6 | 0.268 | 0.192 | 11 | 0.632 | 0.366 |
| 17 | q22 | 18 | 0.274 | 0.882 | 7 | 0.335 | 0.616 | 19 | 0.343 | 0.621 |
| 17 | q23.1 | 20 | 0.747 | 0.841 | 6 | 0.343 | 0.190 | 14 | 0.892 | 0.366 |
| 19 | p13.11 | 27 | 0.961 | 0.384 | 14 | 0.944 | 0.140 | 13 | 0.691 | 0.863 |
| 19 | p13.12 | 18 | 0.853 | 0.343 | 10 | 0.457 | 0.514 | 8 | 0.526 | 0.569 |
| 19 | q12 | 22 | 0.389 | 0.754 | 10 | 0.453 | 0.834 | 12 | 0.490 | 0.527 |
| 19 | q13.11 | 26 | 0.099 | 0.333 | 11 | 0.152 | 0.757 | 15 | 0.290 | 0.303 |
| 19 | q13.12 | 25 | 0.110 | 0.532 | 11 | 0.256 | 0.901 | 14 | 0.218 | 0.461 |
| 19 | q13.2 | 26 | 0.309 | 0.450 | 12 | 0.287 | 0.728 | 14 | 0.649 | 0.437 |
| 19 | q13.31-q13.41 | 20 | 0.378 | 0.628 | 10 | 0.168 | 0.631 | 10 | 0.927 | 0.759 |

TREATMENT SELECTION METHOD AND BIOMARKER INDICATING SELECTION

FIELD

The present invention relates to a biomarker that indicates which, a FOLFOX regimen or a FOLFIRI regimen, is advantageous to select for a patient having colorectal cancer and a selection method of the regimens using the biomarker.

BACKGROUND

According to the guidelines for treatment of colorectal cancer by the Japanese Society for Cancer of the Colon and Rectum, colorectal cancer is categorized into 5 different stages according to the progression of the cancer. As the stages progress, the cancer becomes more advanced. The stages of the cancer are judged by a degree of invasion into the colon wall, the presence of metastasis to lymph nodes, and the presence of metastasis to other organs. The colorectal cancer in a stage IV is most advanced and has spread to other organs. The cancer in such a stage is hardly removed by surgery and usually subjected to a systemic chemotherapy.

As a first-line therapy for such advanced metastatic colorectal cancer, a FOLFOX regimen plus bevacizumab or a FOLFIRI regimen plus bevacizumab is widely recommended. IN those therapies, bevacizumab (BEV) has been developed as a humanized monoclonal antibody against a vascular endothelial growth factor A (VEGF-A) and serves as a drug which inhibits an interaction between VEGF and VEGFR. The drug applied to a vascular endothelial cell in a tumor blood vessel blocks a signal transduction pathway regulated by a vascular endothelial growth factor receptor (VEGFR) to cause a strong angiogenesis inhibitory effect on the tumor blood vessel.

Usefulness of BEV in treating the unresectable recurrent colorectal cancer has been established since BEV was introduced to a clinical field several years ago. A mechanism of pharmacological action of BEV was clear at the time of discovery, and intensive studies have been conducted on a biomarker for an angiogenesis inhibitor, such as BEV, from an early stage of clinical development. However, a simple and noninvasive biomarker, which ensures sufficient reproducibility in conducting clinical trial and shows no discrepancy in measured values between facilities, has not been identified yet to present time.

Similarly, as a predictive factor of effect for the FOLFOX (5-fluorouracil(5-FU)/levofolinate calcium (I-LV) plus oxaliplatin (L-OHP)) regimen and the FOLFIRI (5-fluorouracil (5-FU)/levofolinate calcium (I-LV) plus irinotecan (CPT-11)) regimen, a biomarker, which has been proven to be useful in conducting clinical trial, has not been identified yet to present time.

Patent literature 1 (Japanese Patent Application Laid-Open No. 2011-135838) discloses that the copy number of DNA can be used as a marker for selecting an optimum drug treatment method for an affected patient. This marker can predict the onset and progress of age-related macular degeneration causing a significant vision loss with high accuracy and probability. Thus, this disclosure provides a marker for determining a patient having susceptibility to age-related macular degeneration. The marker can be preferably used for early prevention of age-related macular degeneration and selecting an optimum drug treatment method for an affected patient.

Patent literature 2 (Japanese Patent Application Laid-Open No. 2010-162029) provides an example in which the copy number of DNA is used as a marker for colorectal cancer. This disclosure provides a method of quickly and accurately detecting changes in the copy numbers of genes which may serve as markers for various genetic disorders such as cancer and trisomy with high resolution by combining two very different types of arrays. Examples of diseases to which this method can be applied may include breast cancer, lung cancer, colorectal cancer, testicular cancer, endometrial cancer, and bladder cancer.

Further, Patent literature 3 (Japanese Translation of PCT Patent Application Publication No. 2008-524986) discloses a method in which a change in the copy number of gene is used for diagnosis, prognosis, prediction, prevention, and treatment of breast cancer, ovarian cancer, stomach cancer, colorectal cancer, esophageal cancer, mesenchymal cancer, bladder cancer, or non-small cell lung cancer. More specifically, according to the disclosure, a change in the copy number of gene is used to predict a response of tumorous lesion to various treatment plans including a derivative based on a taxane such as Taxol™ or Taxotere™, or any other taxane.

CITATION LIST

Patent Literature

Patent Literature 1: Japanese Patent Application Laid-Open No. 2011-135838
Patent Literature 2: Japanese Patent Application Laid-Open No. 2010-162029
Patent Literature 3: Japanese Translation of PCT Patent Application Publication No. 2008-524986

SUMMARY

Technical Problem

Patent literature 3 has already disclosed that a gain in the copy number of gene can be used to predict a response to a cancer treatment method. However, this disclosure does not provide a more specific marker that determines which, the FOLFOX regimen or the FOLFIRI regimen, is advantageous to select for an individual patient having colorectal cancer.

It is generally accepted that these regimens have no cross-resistance to each other, thus when one drug therapy has no effect, the other drug therapy can be applied. However, applying another drug therapy after the failure of one drug therapy requires further patience to side effects and an additional treatment cost, putting a large burden on a patient.

Considering that there are over 100,000 colorectal cancer patients in Japan only, identifying a predictive factor for effects of anti-tumor drugs in the FOLFOX regimen and the FOLFIRI regimen to categorize patients to be treated will be beneficial from the point of health economics as a future task. Further, not only from the point of health economics, such a predictive factor also offers other beneficial effects on the patient. For example, the patient can avoid an adverse event caused by administration of a non-effective drug or eliminate a wasteful treatment period in which a non-effective drug is administered. Thus, it is highly needed to predict which, the FOLFOX regime or the FOLFIRI regime, is advantageous for the patient.

Solution to Problem

The present invention was conceived in view of the foregoing problems, and an object of the present invention is to provide a biomarker that indicates which, a FOLFOX regimen or a FOLFIRI regimen, is advantageous for treating a patient on the basis of whether the copy number of a specific region on a human chromosome is gained or not, and a selection method of the regimens.

More specifically, a biomarker according to the present invention indicates which, a FOLFOX regimen or a FOLFIRI regimen, is advantageous for treating a patient having colorectal cancer, the biomarker being characterized by being a gain in the copy number of at least one region among 7p15.3, 7q34, 8q24.1, 8q24.2, 8q24.1-q24.2, 9q34.3, 13q12.2, 13q14.11, 13q22.1, 13q32.2-q32.3, 13q34, 20q12, 20q13.13, 20q13.2, and 20q13.3, on human chromosomes.

Further, the biomarker indicates which, the FOLFOX regimen or the FOLFIRI regimen, is advantageous for treating a patient having colorectal cancer, the biomarker being characterized by being a gain in the copy number of any region among 7q34, 8q24.1, 8q24.2, 8q24.1-q24.2, 9q34.3, 13q12.2, and 13q14.11, on the human chromosomes.

Further, a selection method of regimens according to the present invention selects either a FOLFOX regimen or a FOLFIRI regimen for colorectal cancer, the method being characterized in including the steps of:
measuring a gain in the copy number of a specific region on a human chromosome in a tumor tissue specimen of the colorectal cancer; and
selecting either the FOLFOX regimen or the FOLFIRI regimen on the basis of whether the copy number is gained or not, wherein
the specific region on the human chromosome is at least one region among 7p15.3, 7q34, 8q24.1, 8q24.2, 8q24.1-q24.2, 9q34.3, 13q12.2, 13q14.11, 13q22.1, 13q32.2-q32.3, 13q34, 20q12, 20q13.13, 20q13.2, and 20q13.3.

Further, the selection method of regimens according to the present invention is characterized in that:
the specific region on the human chromosome is at least one region among 7q34, 8q24.1, 8q24.2, 8q24.1-q24.2, 13q12.2, and 13q14.11, and
in the step of selecting either the FOLFOX regimen or the FOLFIRI regimen, the FOLFIRI regimen is selected when the copy number of the specific region is gained.

Further, the selection method of regimens of the present invention is characterized in that:
the specific region on the human chromosome is a 9q34.3 region, and
in the step of selecting either the FOLFOX regimen or the FOLFIRI regimen, the FOLFIRI regimen is selected when the copy number of the specific region is not gained.

Further, the selection method of regimens of the present invention is characterized in that:
the specific regions on the human chromosomes are 7p15.3 and 8q24.1, and
in the step of selecting either the FOLFOX regimen or the FOLFIRI regimen, the FOLFOX regimen is selected when the copy number of the 7p15.3 region is gained and the copy number of the 8q24.1 region is not gained.

Advantageous Effects of Invention

The biomarker and the selection method of regimens according to the present invention enable to select which of regimens, the FOLFOX regimen or the FOLFIRI regimen, both having no statistically significant difference in effects, is advantageous for an individual patient. Accordingly, there is obtained an effect that allows the patient to eliminate the necessity of repeating another regimen after receiving one regimen.

BRIEF DESCRIPTION OF DRAWINGS

FIG. 9 is a diagram showing graphs indicating results (Kaplan-Meyer curves) on chromosome 13.

FIG. 10 is a diagram showing graphs indicating results (Kaplan-Meyer curves) on chromosome 13.

FIG. 11 is a diagram showing graphs indicating results (Kaplan-Meyer curves) on chromosome 20.

FIG. 12 is a diagram showing graphs indicating results (Kaplan-Meyer curves) on chromosome 20.

FIG. 13 is a diagram showing differences (p-values) in OS and PFS between a group having a copy number gain (CNG) and a group having no copy number gain in all patients (154 patients), and differences (p-values) in OS and PFS between a FOLFOX group and a FOLFIRI group in each of 2 groups, a group having CNG indicated by CNG(+) and a group having no CNG indicated by CNG(-), in regions on chromosome 7.

FIG. 14 is a diagram showing differences (p-values) in OS and PFS between the group having a copy number gain (CNG) and the group having no copy number gain in all patients (154 patients), and differences (p-values) in OS and PFS between the FOLFOX group and the FOLFIRI group in each of 2 groups, the group having CNG indicated by CNG(+) and the group having no CNG indicated by CNG (-), in regions on chromosome 8.

FIG. 15 is a diagram showing differences (p-values) in OS and PFS between the group having a copy number gain (CNG) and the group having no copy number gain in all patients (154 patients), and differences (p-values) in OS and PFS between the FOLFOX group and the FOLFIRI group in each of 2 groups, the group having CNG indicated by CNG(+) and the group having no CNG indicated by CNG(−), in regions on chromosomes 13 and 20.

FIG. 19 is a diagram showing graphs indicating PFS and OS plotted by Kaplan-Meier curves in groups categorized on the basis of the status of CNG in the 7p15.3 and 8q24.1 regions.

FIG. 20 is a diagram showing graphs indicating PFS and OS plotted by Kaplan-Meier curves in groups categorized on the basis of the status of CNG in the 7p15.3 and 8q24.1 regions.

FIG. 21 is a diagram showing differences (p-values) in OS and PFS between the group having a copy number gain and the group having no copy number gain in all patients (154 patients), the FOLFOX group (75 patients), and the FOLFIRI group (79 patients) in chromosomal amplification regions other than those on chromosomes 7, 8, 13, and 20.

DESCRIPTION OF EMBODIMENTS

Figure 1A:
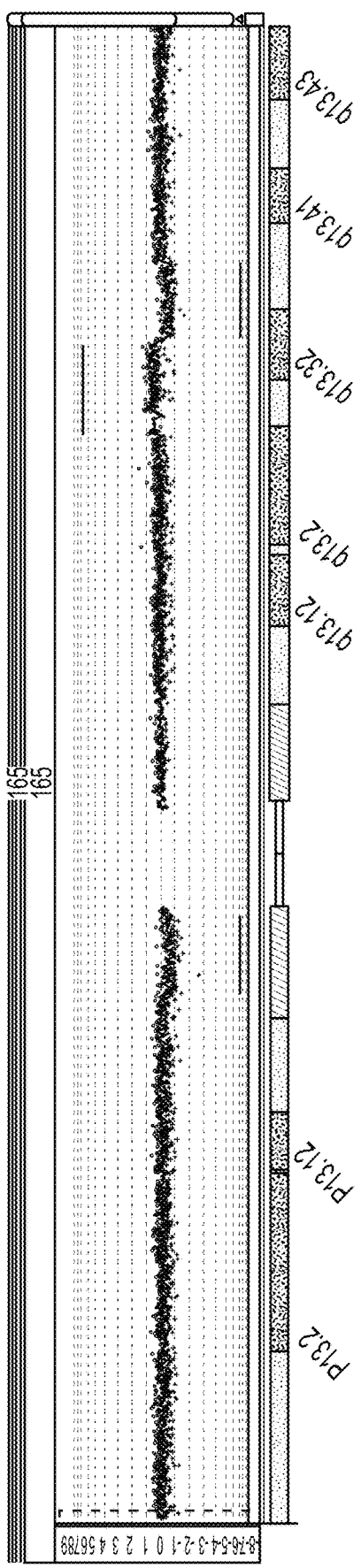
FIG. 1 is a diagram showing an entire region of a chromosome and an exemplary list of genes encoded in various regions, using a Genomic Workbench™ 6.5 Lite software manufactured by Agilent™.

Hereinafter, a biomarker and a selection method of regimens according to the present invention will be described with reference to the drawings and Examples. Note that the foregoing description exemplifies one embodiment and one Example of the present invention and the present invention is not limited to the following description. The following description may be changed or modified within a scope not departing from the gist of the present invention.

A chemotherapy used in a stage IV includes a FOLFOX regimen and a FOLFIRI regimen. The FOLFOX regimen is a regimen in which 3 drugs, fluorouracil (5-fluorouracil (5-FU)), folinic acid (levofolinate calcium (l-LV)), and oxaliplatin (L-OHP) are used in combination. The FOLFOX regimen may be further used in combination with bevacizumab (BEV).

The FOLFIRI regimen is a regimen in which 3 drugs, fluorouracil (5-fluorouracil (5-FU)), folinic acid (levofolinate calcium (l-LV)), and irinotecan hydrochloride (irinotecan (CPT-11)) (hereinafter simply referred to as "irinotecan"), are used in combination. The FOLFIRI regimen may be further used in combination with bevacizumab (BEV).

Thus, a difference between the FOLFOX regimen and the FOLFIRI regimen lies on whether oxaliplatin or irinotecan is used. However, it has been conventionally difficult to predict which of the regimens is suitable for an individual patient. As describe in Examples below, the present invention makes it possible to determine which of the regimens is advantageous to select by examining a gain in the copy number of a specific region on a human chromosome using chromosomes in a tumor tissue specimen derived from a patient.

Note that the term "advantageous" in the description is used to mean that a longer survival period can be expected with high probability after treatment. Further, in the description, the gain in the copy number of a specific region on a human chromosome can be measured by a method, such as a CGH method, a PCR method, and a RT-PCR method, described below.

EXAMPLE

Example 1

Cases used in Example below were subjected to a first-line chemotherapy for unresectable recurrent colorectal cancer registered to "a randomized comparative phase III trial (WJOG4407G) of a 5-fluorouracil (5-FU)/levofolinate calcium (l-LV) plus oxaliplatin (L-OHP)) plus bevacizumab (BEV) combination regimen versus a 5FU/I-LI plus irinotecan (CPT-11) plus BEV combination regimen in a first-line chemotherapy for unresectable recurrent colorectal cancer" in West Japan Oncology Group from September 2008 to December 2012. Data were obtained from patients who gave informed consent to WJOG4407GTR.

As a specimen, a tumor tissue specimen obtained before treatment was used to create a pathology slide (an FFPE slide). The tumor tissue specimen, which was a surgical specimen or an endoscopic biopsy specimen, was paraffin embedded, sliced into 5 μm thin layers, and fixed on a glass slide to prepare a slide. Thus, a step of collecting the tumor tissue specimen includes collecting a specimen during surgery or collecting a biopsy tissue by an endoscope. Note that a specimen collected prior to the registration of clinical trial was also used.

A change in the copy number of a specific region on a human chromosome in the tumor tissue was measured by using a comparative genomic hybridization (CGH) method. The CGH method detects an abnormality in the copy number of genomic DNA, such as gain, loss, and amplification, from all chromosomes in a short time. The CGH method capable of detecting a change in the copy number of chromosome is currently widely used as a method for analyzing genome abnormality in a solid tumor, which has been difficult to analyze in detail by a conventional chromosome analysis method.

The present technique can detect loss, gain, and amplification of the copy number, which change the physical size of the chromosome, but fails to detect a balanced chromosomal translocation not causing a change in the copy number. For example, translocation or the like does not change the copy number of the chromosome and is thus undetectable.

A cancer-related gene located in a newly identified amplification region is likely to be more expressed due to a gene amplification. Thus, the CGH analysis is frequently performed to search such a gene as a new target for cancer treatment. In the present studies, genomic DNA was extracted from a paraffin section and an analysis was performed by competing such genomic DNA with commercially available DNA derived from a normal tissue.

Procedures of the CGH analysis are as follows. First, DNA was extracted from an FFPE slide specimen. In total, 154 DNA samples were extracted.

Next, DNA extracted from a cancer site was prepared for fluorescent labelling and hybridization. Specifically, the DNA extracted from a cancer site was fluorescently labelled by cyanine 5 (Cy5), and reference DNA (DNA from a normal tissue) was fluorescently labelled by cyanine 3 (Cy3).

Hybridization was performed as follows. In a processed sample (Cy5-labelled DNA from a cancer site plus Cy3-labelled reference DNA) having a total volume of 110 μl, 100 μl was applied to a gasket slide glass corresponding to a 4×44K format of a CGH microarray manufactured by Agilent™. Next, the gasket slide glass was overlaid on a surface of a 4×44K microarray slide glass coated with probes. Two slides were then fixed to a chamber. A hybridization reaction was performed in a rotary type oven at 65° C. for 40 hours.

Actual analysis was performed as follows. First, the double-layered gasket and array slides were separated by inserting tweezers. The array slide was inserted in a slide rack in a glass container filled with a CGH washing buffer 1 manufactured by Agilent™. The slide was then left at the room temperature for 5 minutes.

Next, the array was transferred with the slide rack to another glass container filled with a CGH washing buffer 2 manufactured by Agilent™. The slide was then left at 37° C. for 1 minute.

Next, the array was taken out and set to a slide holder. The slide holder was then set to a scanner equipped with an ozone removal filter manufactured by Agilent™ to scan the array.

A scan control software manufactured by Agilent™ was started in a personal computer (PC) to fetch an array image.

Next, fluorescence intensity of Cy3 and Cy5 at probe-bound spots (about 44,000 spots) on the array was obtained from the previously fetched image using a Feature Extraction software manufactured by Agilent™. A log 2 ratio of Cy5/Cy3 was calculated at each spot (corresponding to a particular locus on a chromosome) to estimate whether the copy number of the specific region on the human chromosome corresponding to the spot is gained or not.

A gain in the copy number of a specific region on a human chromosome is referred to as an aberration. A Genomic Workbench™ 6.5 Lite software manufactured by Agilent™ was used to analyze on which chromosomes and in which regions aberrations exist. Data created by this software were shown, as an example, in FIG. 1(a) (a panel showing an entire region of a chromosome) and FIG. 1(b) (a table showing a list of genes encoded in various chromosomal regions). Such data allow users to find locations of aberrations on all chromosomes in each case.

The table in FIG. 1 (FIG. 1(b)) includes information on a sample name, a chromosome number, a locus, amplification or loss, gene names located in each locus, and the like. In the present Example, chromosomes and loci of aberrations were recorded in all 154 specimens. This time, in particular, the search was narrowed to the loci having a log 2 ratio of Cy5/Cy3 of greater than 0.25, that is, the loci amplified by $2^{0.25}=1.19$ times or more compared to normal loci. Examining a gain/loss of the copy number by comparing with a normal tissue in this manner constitutes a step of measuring a gain in the copy number of a specific region on a human chromosome in a tumor tissue specimen of colorectal cancer.

Note that the amplification ratio was not necessarily set to an integer multiple and instead set to 1.19, for example, in this Example by assuming heterogeneity in a cell of the tumor tissue from which DNS was isolated, caused by contamination of a normal cell, nonuniformity of the tumor cell, or the like.

Further, the copy numbers of almost all human genes in all tissues can be easily measured by using a "Taqman™ Copy Number Assay" manufactured by Life Technologies.

In this Example, the CGH analysis was performed with an "Agilent Oligo CGH Microarray Kit" manufactured by Agilent™ using the cancer site genomic DNA extracted from a paraffin embedded section of a surgical specimen before treatment or a biopsy specimen (an endoscopic biopsy tissue) isolated from 154 colorectal cancer patients subjected to either of 2 combination therapies, (1) a FOLFOX regimen plus bevacizumab or (2) a FOLFIRI regimen plus bevacizumab. Note that an observation period of the patients was 1,600 days.

A cutoff value for a gain in the copy number of a specific region on a human chromosome was set to greater than 0.25 in the log 2 ratio to search regions amplified about 1.2 times or more of the original copy number, that is, regions having 2.4 copies or more. As a result, amplification regions were concentrated on chromosomes 7, 8, 13, and 20 in many cases. Table 1 shows the regions of which the amplification was observed in 30 cases or more.

TABLE 1

| Chr | locus | CASES | PFS (p-VALUE) | OS (p-VALUE) |
|---|---|---|---|---|
| 7 | q11.21 | 37 | 0.51 | 0.0027 |
| 7 | q11.22-23 | 44 | 0.26 | 0.0029 |
| 7 | q34 | 35 | 0.37 | 0.0069 |
| 7 | q36.2 | 34 | 0.74 | 0.0068 |
| 8 | p11.1 | 35 | 0.71 | 0.46 |
| 8 | p11.23 | 31 | 0.78 | 0.69 |
| 8 | q22.2 | 52 | 0.16 | 0.63 |
| 8 | q24.2 | 63 | 0.26 | 0.36 |
| 13 | q12.2 | 74 | 0.36 | 0.0097 |
| 13 | q14.11 | 64 | 0.26 | 0.0197 |
| 13 | q22.1 | 67 | 0.35 | 0.0289 |
| 13 | q32.2-q32.3 | 66 | 0.25 | 0.0127 |
| 13 | q34 | 64 | 0.33 | 0.0246 |
| 20 | p13 | 43 | 0.64 | 0.0011 |
| 20 | p12.1-p11.23 | 44 | 0.77 | 0.0015 |
| 20 | p11.2 | 52 | 0.81 | 0.0027 |
| 20 | q12 | 97 | 0.67 | 0.0056 |
| 20 | q13.13 | 101 | 0.56 | 0.0091 |
| 20 | q13.2 | 105 | 0.79 | 0.0096 |
| 20 | q13.3 | 84 | 0.57 | 0.0183 |

In Table 1, "Chr" indicates a chromosome number and "locus" indicates a gene locus. A log-rank test was performed in progression-free survival (PFS) and overall survival (OS) between two groups, a group of cases (patients) having a copy number gain in these regions and a group of cases (patients) having no copy number gain, in these regions. As a result, there was no significant difference in PFS in all regions. However, a significant difference was observed (p<0.05) in OS in all regions except for those on chromosome 8. It is suggested that the specific region on the human chromosome having a significant difference in OS, such as those described above, may include a prognostic factor. In Table 1, the specific regions on the human chromosomes having a significant difference in OS were printed with an underline.

Figure 2:
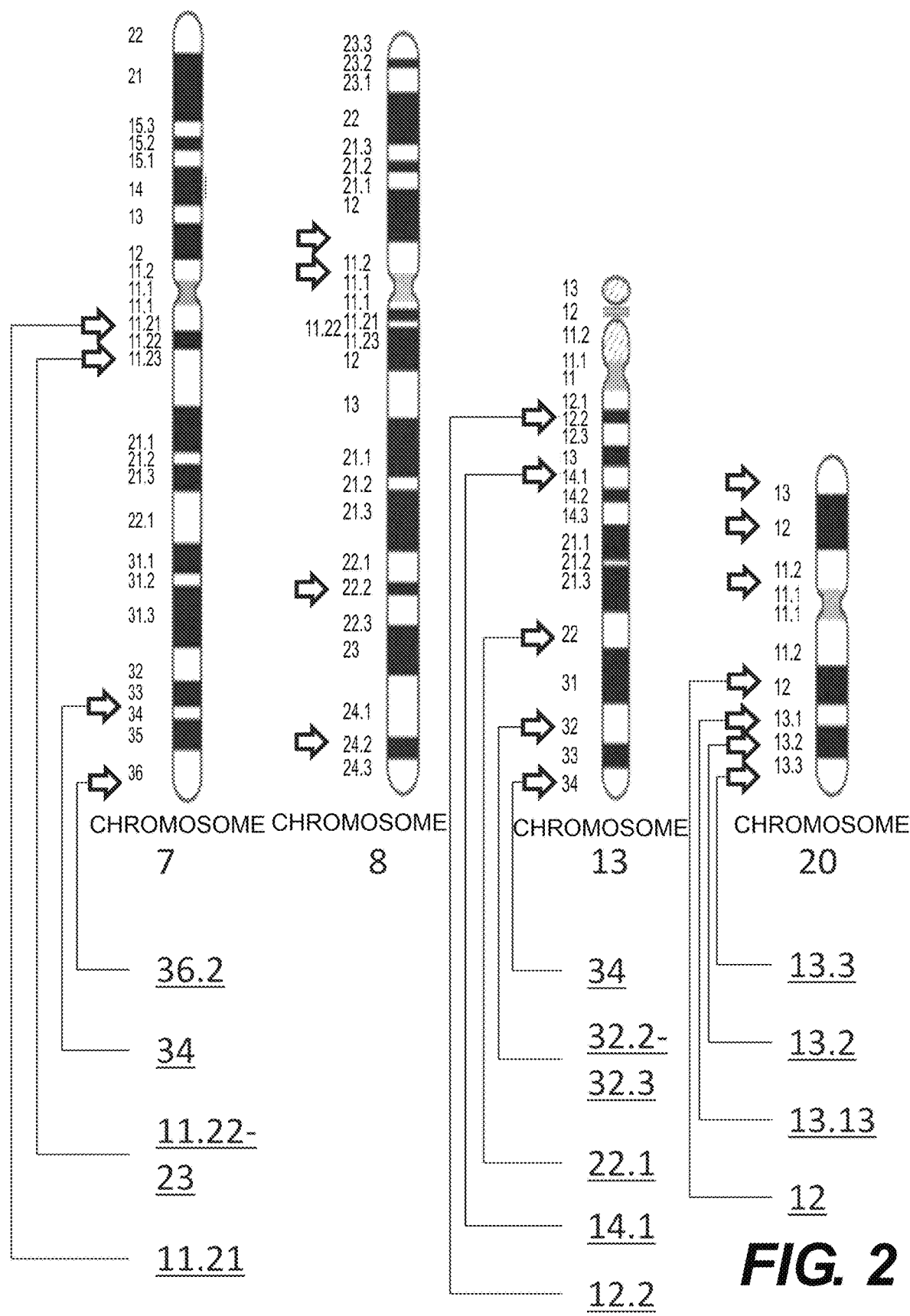
FIG. 2 is a diagram showing locations of amplification regions on chromosomes 7, 8, 13, and 20.

FIG. 2 shows locations of amplification regions on chromosomes 7, 8, 13, and 20. The amplification regions are indicated by arrows. The actual amplification regions may be shifted to some degree from the center of those regions. Note that region numbers of long arms of chromosomes 7, 13, and 20 were indicated by leading lines.

Figure 3:
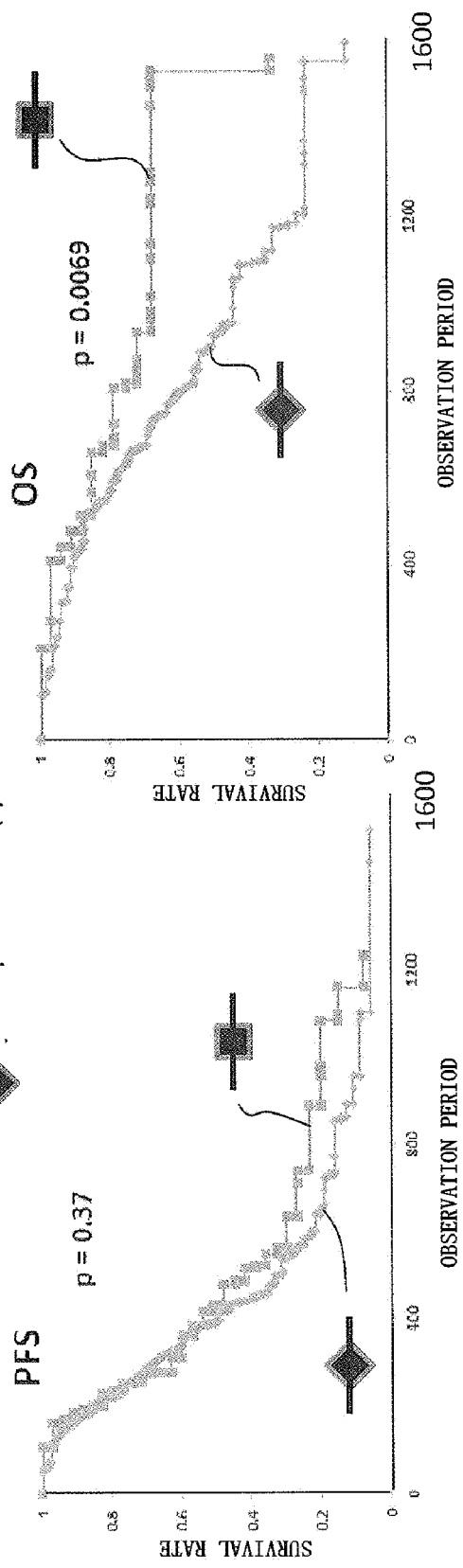
FIG. 3 is a diagram showing graphs indicating survival curves based on whether the copy number of a long arm 34 region of chromosome 7 (7q34) is gained or not.

Among those regions, FIG. 3 shows results (survival curves) in the long arm 34 region of chromosome 7 (7q34).

FIG. 3(a) shows a result of PFS, while FIG. 3(b) shows a result of OS. In both FIGS. 3(a) and (b), a lateral axis indicates an observation period (daily unit from day 0 to 1,600) and a longitudinal axis indicates a survival rate (arbitrary unit from 0 to 1). Further, the survival rates of patients having amplification (Amplification+) in these regions are indicated by square marks and the survival rates of patients having no amplification (Amplification−) in these regions are indicated by rhombic marks. The patients having amplification (amplification+) in this region had significantly more favorable prognosis in terms of OS than the patients having no amplification (amplification−).

Figure 4:
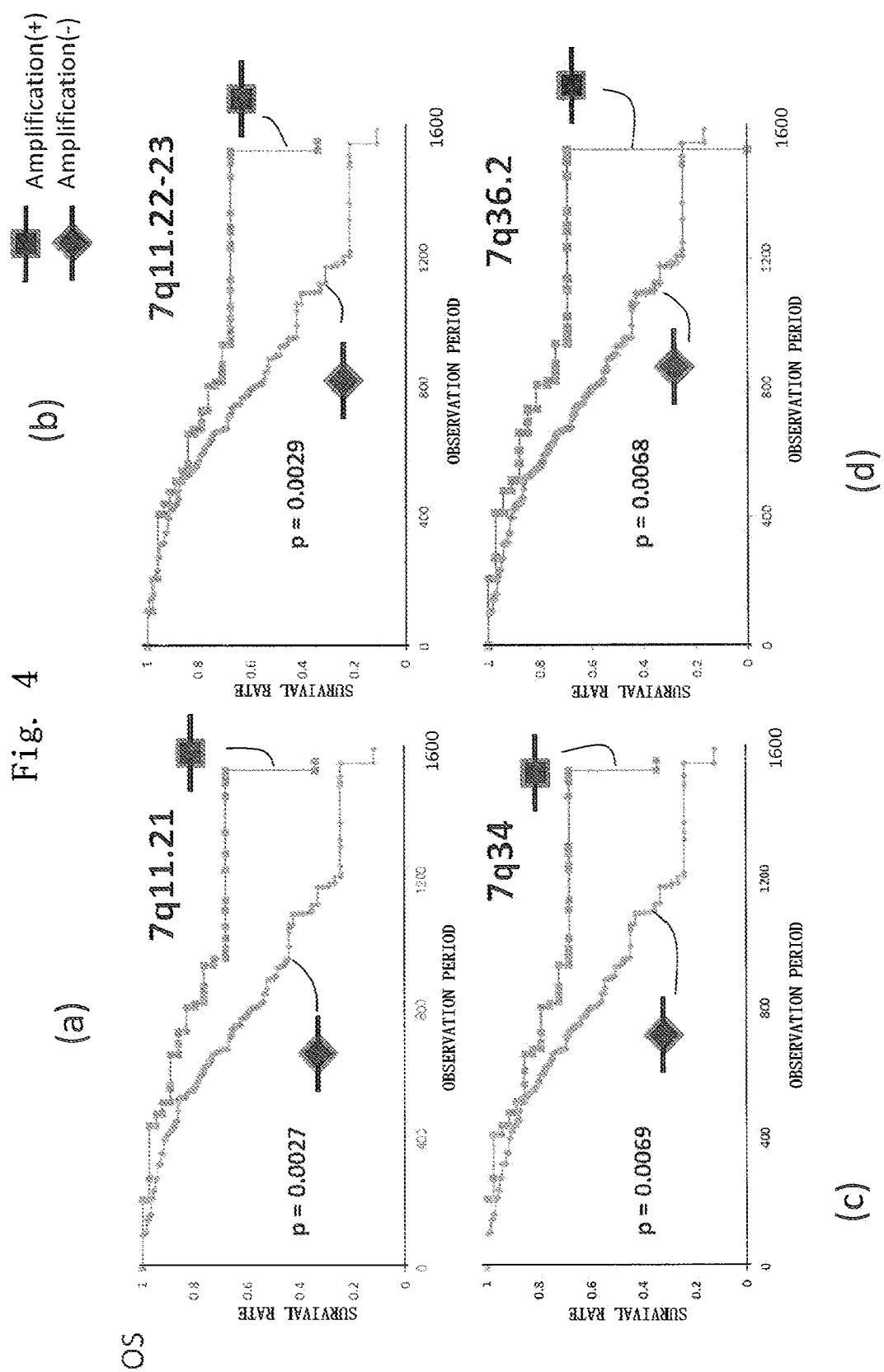
FIG. 4 is a diagram showing graphs indicating survival curves based on whether the copy numbers of 4 amplification regions in total on the long arm of chromosome 7 are gained or not.

FIG. 4 shows graphs in 4 amplification regions in total located on the long arm of chromosome 7. FIG. 4(a) shows a graph in 7q11.21, FIG. 4(b) in 7q11.22-23, FIG. 4(c) in 7q34, and FIG. 4(d) in 7q36.2. In all graphs, a lateral axis indicates an observation period (daily unit from day 0 to 1,600) and a longitudinal axis indicates a survival rate (arbitrary unit from 0 to 1). Further, the survival rates of patients having amplification (Amplification+) in these regions are indicated by square marks and the survival rates of patients having no amplification (Amplification−) in these regions are indicated by rhombic marks. In all regions, the patients having amplification had significantly more favorable prognosis in terms of OS than the patients having no amplification. Further, these regions are located on the same arm (long arm) of the same chromosome, and thus combinations of the patients allocated to the amplification groups and the no amplification groups are similar to each other between the regions. As a result, their graphs also exhibit similar curves.

Figure 5:
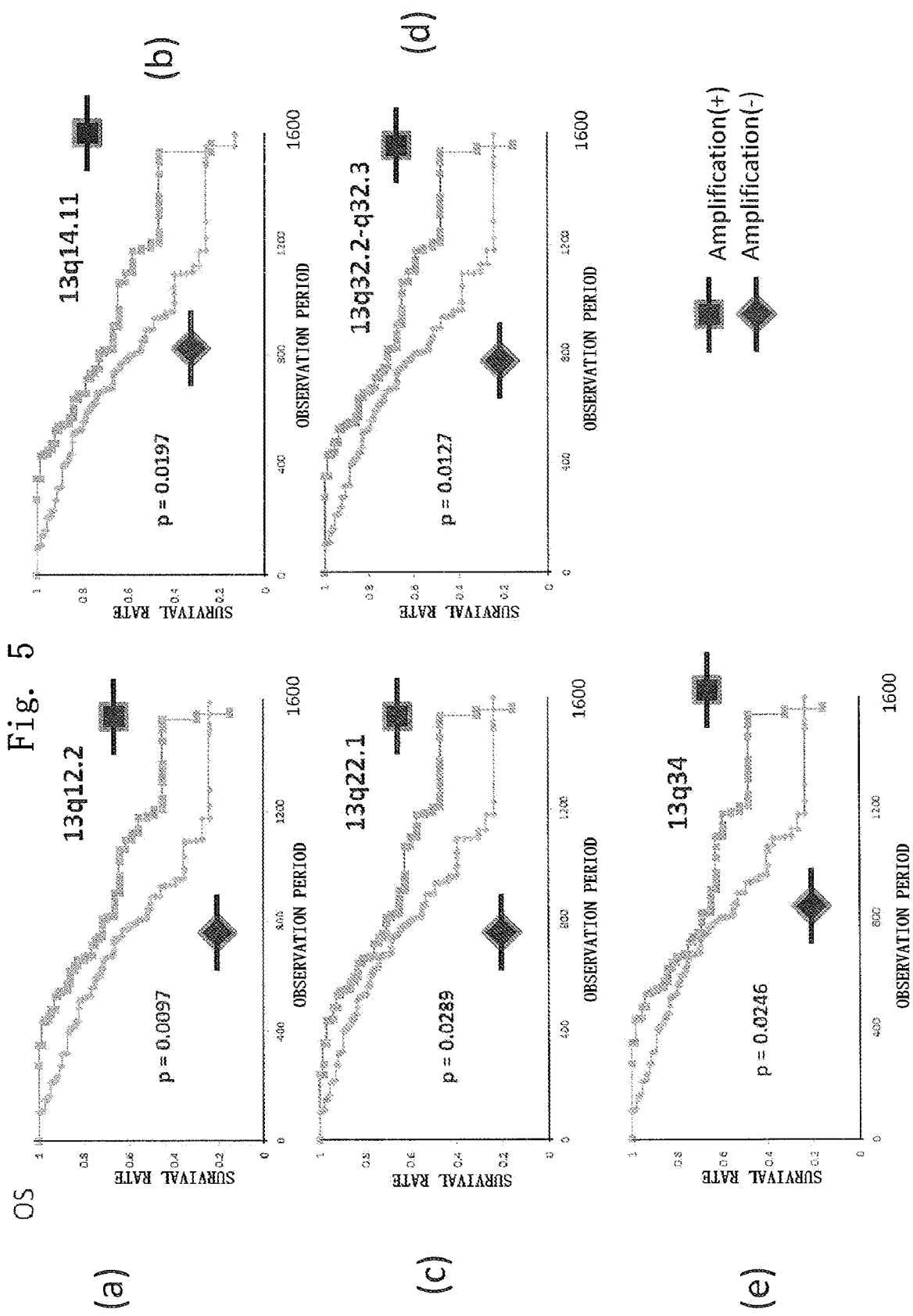
FIG. 5 is a diagram showing graphs indicating survival curves based on whether the copy numbers of 5 amplification regions on a long arm of chromosome 13 are gained or not.
Figure 6:
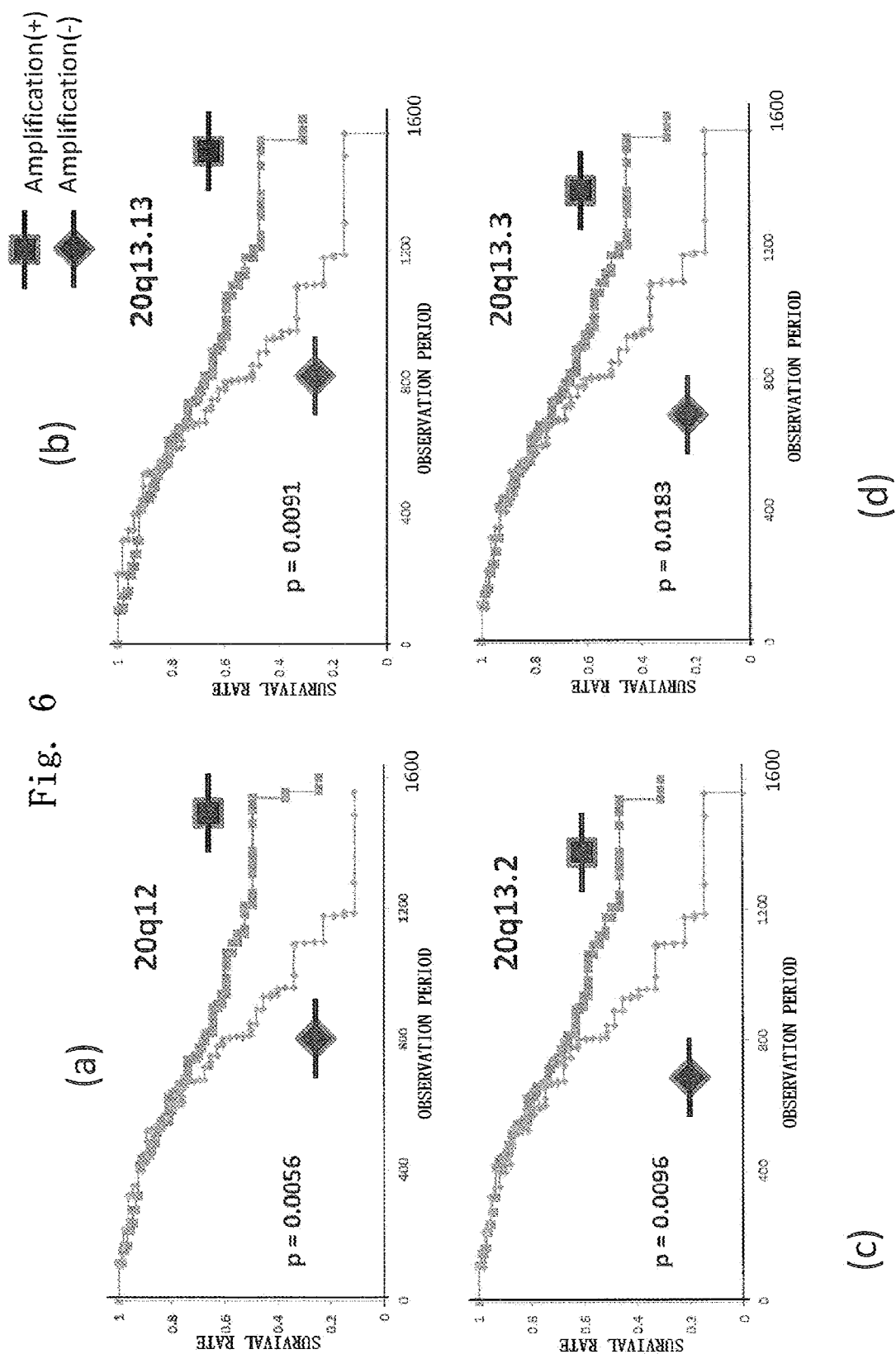
FIG. 6 is a diagram showing graphs indicating survival curves based on whether the copy numbers of 4 amplification regions on a long arm of chromosome 20 are gained or not.

FIG. 5 and FIG. 6 show results (survival curves) of OS on chromosome 13 and chromosome 20, respectively. FIGS. 5(a) to 5(e) show results in amplification regions including 13q12.2, 13q14.11, 13q22.1, 13q32.2-q32.3, and 13q34, respectively. Further, FIGS. 6(a) to 6(d) show results in amplification regions including 20q12, 20q13.13, 20q13.2, and 20q13.3, respectively.

In all graphs, a lateral axis indicates an observation period (daily unit from day 0 to 1,600) and a longitudinal axis indicates a survival rate (arbitrary unit from 0 to 1). Further, the survival rates of patients having amplification (Amplification+) in these regions are indicated by square marks and the survival rates of patients having no amplification (Amplification−) in these regions are indicated by rhombic marks. In all amplification regions on these chromosomes, the patients having amplification had more favorable prognosis. Further, the survival rate curves were similar to each other between the regions on the same arm of chromosome, specifically, on the long arm of chromosome 13 and on the long arm of chromosome 20.

Next, an effect on early tumor shrinkage (ETS) was examined. The size of a tumor at the time of registration, that is, the original size, was compared with the size of the tumor after 8 weeks from the registration to obtain a difference in percentage terms. Average values of the difference were obtained in two groups, a group of cases having amplification and a group of cases having no amplification, and a difference between the average values was examined by a t-test in each chromosomal region.

Results are shown in Table 2. In Table 2, the specific regions on the human chromosomes in which the test result of ETS was less than 5% were printed with an underline. Further, p-values indicating a significant difference in OS were also printed with an underline. Results of ETS are shown in FIG. 7.

TABLE 2

| Chr | locus | CASES | OS (p-VALUE) | ETS |
|---|---|---|---|---|
| 7 | q11.21 | 37 | 0.0027 | 0.1259 |
| 7 | q11.22-23 | 44 | 0.0029 | 0.1390 |
| 7 | q34 | 35 | 0.0069 | 0.0044 |
| 7 | q36.2 | 34 | 0.0068 | 0.1610 |
| 13 | q12.2 | 74 | 0.0097 | 0.00032 |
| 13 | q14.11 | 64 | 0.0197 | 0.00019 |
| 13 | q22.1 | 67 | 0.0289 | 0.00022 |
| 13 | q32.2-q32.3 | 66 | 0.0127 | 0.00067 |
| 13 | q34 | 64 | 0.0246 | 0.00226 |
| 20 | p13 | 43 | 0.0011 | 0.1046 |
| 20 | p12.1-p11.23 | 44 | 0.0015 | 0.1084 |
| 20 | p11.2 | 52 | 0.0027 | 0.0736 |
| 20 | q12 | 97 | 0.0056 | 0.0027 |
| 20 | q13.13 | 101 | 0.0091 | 0.0098 |
| 20 | q.13.2 | 105 | 0.0096 | 0.0052 |
| 20 | q13.3 | 84 | 0.0183 | 0.0028 |

Figure 7:
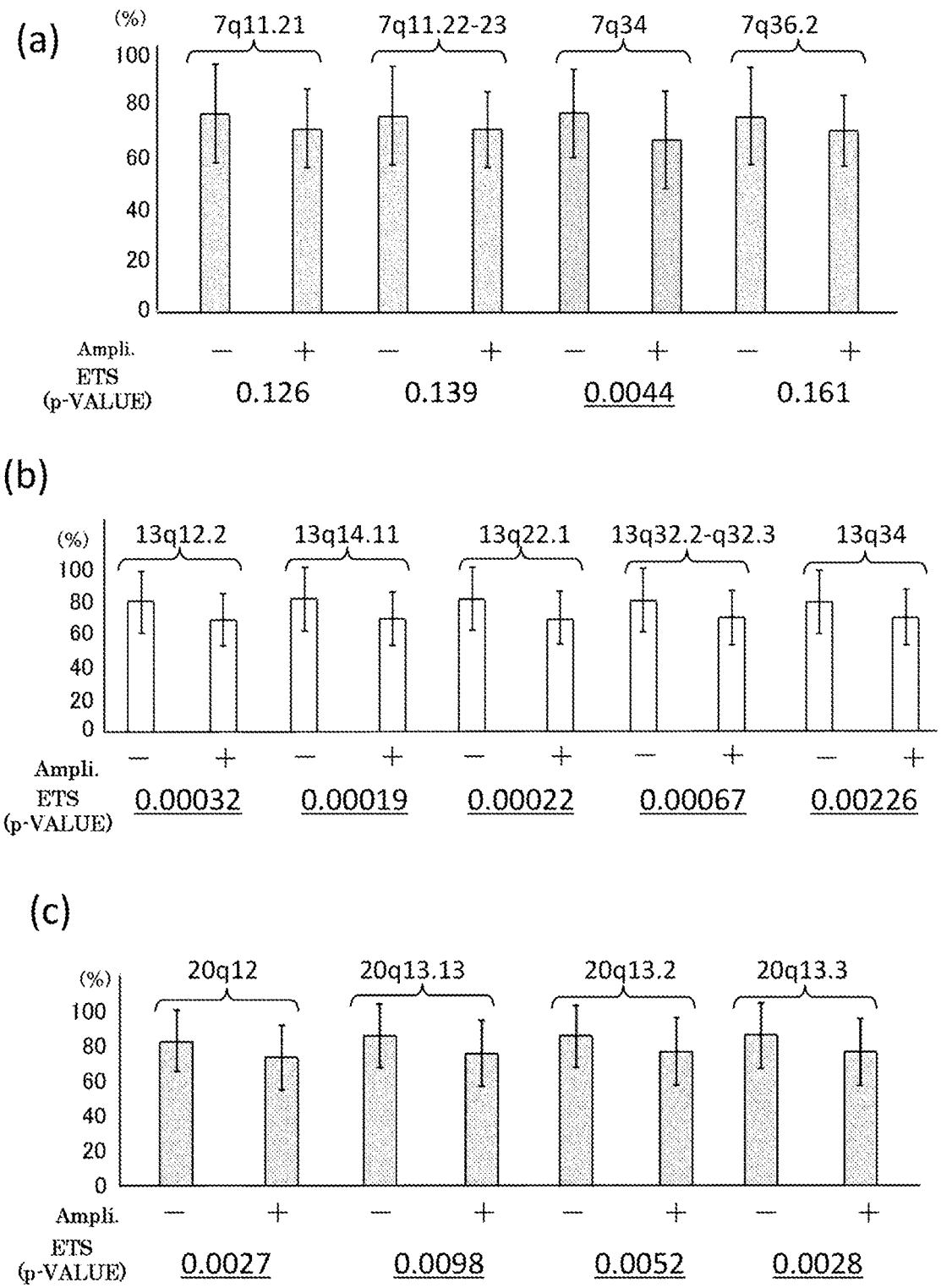
FIG. 7 is a diagram showing graphs indicating results of early tumor shrinkage (ETS) in the amplification regions on chromosomes 7, 13, and 20.

FIG. 7 shows results of ETS on respective chromosomes 7 (FIG. 7(a)), 13 (FIG. 7(b)), and 20 (FIG. 7(c)). In each figure, a lateral axis indicates the presence or absence of amplification (Amplification±) of respective chromosomes and p-values of ETS. A longitudinal axis indicates a ratio (%) of the size of the tumor compared to that at the time of registration. Note that p-values less than 5% were printed with an underline.

As shown in FIG. 7(a), a significant difference was observed in ETS in one location (q34) on the long arm of chromosome 7. Further, as shown in FIG. 7(b), a significant difference was observed in ETS in all 5 locations (q12.2, q14.11, q22.1, q32.2-q32.3, and q34) on the long arm of chromosome 13. As shown in FIG. 7(c), a significant difference was observed in ETS in 4 locations (q12, q13.13, q13.2, and q13.3) on the long arm of chromosome 20 (no significant difference was observed in 3 locations on the short arm). That is, a significant difference was observed in ETS in total of 10 regions. What is significant here is that a significant tumor shrinkage was observed in the group of cases in which the copy number of the specific region on the human chromosome was gained. This is consistent with the results (shown in FIG. 3 to FIG. 6) showing favorable prognosis in terms of OS in the group of cases in which amplification was observed.

Thus, it is conceivable that a total of 10 chromosomal regions described above, exhibiting a significant difference not only in OS but also in ETS, include a predictive factor for an effect of the multidrug combination chemotherapy, (1) the FOLFOX regimen plus bevacizumab or (2) the FOLFIRI regimen plus bevacizumab.

Specifically, it is shown that performing the FOLFOX regimen or the FOLFIRI regimen is advantageous to a patient if the copy number of at least one chromosomal region is gained among the 10 regions on chromosomes 7, 13, and 20 described above. In other words, a gain in the copy number of the specific region on the human chromosome can be used as a marker that indicates whether performing the FOLFOX regimen or the FOLFIRI regimen is advantageous. Further, as a gain in the copy number, it is sufficient that the copy number is amplified to at least 2.4 copies or more compared to a normal tissue.

Results are described below for determining whether there is any region in which a therapeutic effect is different between two combination therapies, (1) and (2).

FIG. 8 to FIG. 12 show results (Kaplan-Meier curves) of comparison in OS by a log-rank test between a total of 4 groups: (1) a FOLFOX group applied with the FOLFOX regime plus bevacizumab, 75 cases; (2) a FOLFIRI group applied with the FOLFIRI regime plus bevacizumab, 79 cases; and each group further subdivided into two groups according to the presence or absence of amplification, in the 10 regions (7q34, 13q12.2, 13q14.11, 13q22.1, 13q32.2-q32.3, 13q34, 20q12, 20q13.13, 20q13.2, and 20q13.3) having a significant difference both in OS and ETS. In FIG. 8 to FIG. 12, p-values less than 5% (0.05) were printed with an underline.

Figure 8:
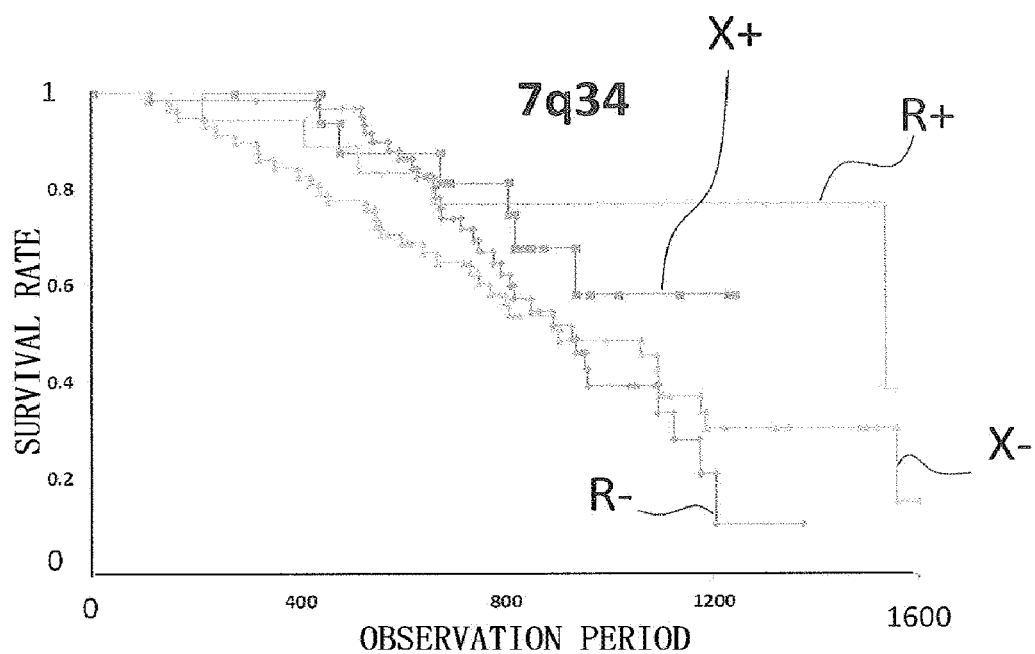
FIG. 8 is a diagram showing results (Kaplan-Meyer curves) of comparison in OS by a log-rank test in the 7q34 region, in which a significant difference is observed both in OS and ETS, conducted among 4 groups: (1) a FOLFOX group applied with the FOLFOX regimen plus bevacizumab, 75 cases; (2) a FOLFIRI group applied with the FOLFIRI regimen plus bevacizumab, 79 cases; and each group further subdivided into two groups according to the presence or absence of amplification.

In FIG. 8, a lateral axis indicates an observation period (daily unit from day 0 to 1,600) and a longitudinal axis indicates a survival rate (arbitrary unit from 0 to 1). The group of the FOLFOX regimen plus bevacizumab having amplification in the copy number of the specific region on the human chromosome is indicated by "X+", the group of the FOLFOX regimen plus bevacizumab having no amplification is indicated by "X−", the group of the FOLFIRI regimen plus bevacizumab having amplification is indicated by "R+", and the group of the FOLFIRI regimen plus bevacizumab having no amplification is indicated by "R−". FIG. 9 to FIG. 12 below use the same annotation.

Referring to FIG. 8, it is shown that a difference in an effect between the group of cases with amplification and the group of cases with no amplification is larger in the FOLFIRI group (R+ and R−) than the FOLFOX group (X+ and X−) in q34 of chromosome 7. A significant difference between R+ and R− in the FOLFIRI regimen group is also proven by having a p-value of 0.0128 (p=0.0128). Thus, this region may include a gene that increases a sensitivity to irinotecan without affecting a sensitivity to oxaliplatin.

Common genes (included in 7q34 and amplified) in the group of cases (35 cases) having amplification in the copy number in this region (7q34) are HIPK2, TBXAS1, PARP12, JHDM1D, LOC100134229, SLC37A3, RAB19, and MKRN1 (see Table 3 below).

Either the FOLFOX regimen or the FOLFIRI regimen can be selected by determining the amplification of 7q34. How- ever, it may also be possible to select either the FOLFOX regimen or the FOLFIRI regimen by measuring the copy numbers of the above-mentioned genes included in 7q34.

FIG. 9 and FIG. 10 show results on chromosome 13. As shown in FIG. 9 and FIG. 10, a larger difference between the groups with and without amplification was observed in the FOLFIRI group also on chromosome 13. Moreover, when comparing between the groups having amplification, the FOLFIRI group tended to have a higher sensitivity than the FOLFOX group (with a p-value of about 0.2). Thus, this region may also include a gene that increases a sensitivity to irinotecan without affecting a sensitivity to oxaliplatin.

A difference between irinotecan and oxaliplatin was remarkably shown particularly in 3 regions of 13q12.2, 13814.11, and 13q22.1.

Common genes (included in 13q12.2 and amplified) in the group of cases (74 cases) having amplification in the copy number in the 13q12.2 region are the following 21 genes: USP12, RPL21, RPL21P28, SNORD102, SNORA27, RASL11A, GTF3A, MTIF3, LNX2, POLR1D, GSX1, PDX1, ATP5EP2, CDX2, PRHOXNB, FLT3, LOC100288730, PAN3, FLT1, POMP, and SLC46A3 (see Table 3 below).

Further, common genes (included in 13q14.11 and amplified) in the group of cases (64 cases) having amplification in the copy number in the 13q14.11 region are the following 27 genes: LOC646982, FOXO1, MIR320D1, MRPS31, SLC25A15, SUGT1L1, MIR621, ELF1, WBP4, KBTBD6, KBTBD7, MTRF1, NAA16, OR7E37P, C13orf15, KIAA0564, DGKH, AKAP11, TNFSF11, C13orf30, EPSTI1, DNAJC15, ENOX1, CCDC122, C13orf31, LOC121838, and SERP2 (see Table 3 below).

Common genes (included in 13q22.1 and amplified) in the group of cases (67 cases) having amplification in the copy number in the 13q22.1 region are the following 2 genes: PIFB1 and KLF5 (see Table 3 below).

Either the FOLFOX regimen or the FOLFIRI regimen can be selected by determining the amplification in the copy numbers of 13q12.2, 13q14.11, and 13q22.1. However, it may also be possible to select either the FOLFOX regimen or the FOLFIRI regimen by measuring the copy numbers of the above-mentioned genes included in these 3 regions.

FIG. 11 and FIG. 12 show results on chromosome 20. As shown in FIG. 11 and FIG. 12, a similar tendency was observed on chromosome 20. However, the FOLFOX group also tended to have a difference in the effect between the groups with and without amplification (X+ vs. X−; p=0.06 to 0.2). Thus, these 4 regions are unlikely to include a gene that specifically affects a sensitivity to either oxaliplatin or irinotecan.

In summary, as a biomarker for differentiating the effects of 2 combination therapies, the following 4 regions can be mentioned: 7q34, 13q12.2, 13q14.11, and 13q22.1. Genes included in these 4 amplification regions shown in Table 3 may also be mentioned as a candidate of such a biomarker.

TABLE 3

| 7q34 | HIPK2 | TBXAS1 | PARP12 | JHDM1D | LOC100134229 | SLC37A3 | RAB19 | MKRN1 | |
|---|---|---|---|---|---|---|---|---|---|
| 13q12.2 | USP12 | RPL21 | RPL21P28 | SNORD102 | SNORA27 | RASL11A | GTF3A | | |
| | MTIF3 | LNX2 | POLR1D | GSX1 | PDX1 | ATP5EP2 | CDX2 | | |
| | PRHOXNB | FLT3 | LOC10028873C | PAN3 | FLT1 | POMP | SLC46A3 | | |
| 13q14.11 | LOC646982 | FOXO1 | MIR320D1 | MRPS31 | SLC25A15 | SUGT1L1 | MIR621 | ELF1 | WBP4 |
| | KBTBD6 | KBTBD7 | MTRF1 | NAA16 | OR7E37P | C13orf15 | KIAA0564 | DGKH | AKAP11 |
| | TNFSF11 | C13orf30 | EPSTI1 | DNAJC15 | ENOX1 | CCDC122 | C13orf31 | LOC121838 | SERP2 |
| 13q22.1 | PIBF1 | KLF5 | | | | | | | |

It is expected that a predictive factor (gene) for effect can be found by over-expressing or knocking down by siRNAs these candidate genes shown in Table 3 in a colorectal cancer cell line and measuring a change in sensitivity to irinotecan and oxaliplatin. It is also possible to predict which of the regimens is advantageous as a combination drug with bevacizumab to an individual patient having colorectal cancer by measuring the copy numbers (expression levels) of the genes shown in Table 3.

Further, without identifying such a predictive factor (gene) for effect, it is still possible to predict that performing the FOLFIRI regimen is more therapeutically effective for the patient who has amplification in the copy number of at least one of the 4 regions including 7q34, 13q12.2, 13q14.11, and 13q22.1.

A difference between irinotecan and oxaliplatin was remarkably shown particularly in 3 regions including 13q12.2, 13814.11, and 13q22.1. Thus, it is possible to predict that performing the FOLFIRI regimen is advantageous to a patient with high probability by examining a gain in the copy number of at least one of these 3 regions in the patient.

Further, a difference between the FOLFOX regimen and the FOLFIRI regimen lies on whether oxaliplatin or irinotecan is used. Thus, amplification in the copy number of any of these 4 regions including 7q34, 13q12.2, 13q14.11, and 3q22.1, can be used as a marker to predict a therapeutic effect of irinotecan.

Note that, as a gain in the copy number, it is sufficient that the copy number is amplified to at least 2.4 copies or more compared to a normal tissue.

Example 2

Next, results are described below for summarizing data obtained in an observation period of up to 70 months from the patients who gave informed consent to WJOG4407GTR as described in Example 1. Having the observation period longer than that in Example 1 led to results with higher accuracy.

Similar to Example 1, a cutoff value in amplification in the copy number of a specific region on a human chromosome was set to greater than 0.25 in the log 2 ratio to search a region amplified about 1.2 times or more of the original copy number, that is, a region having 2.4 copies or more. As a result, amplification regions were concentrated on chromosomes 7, 8 (long arm), 13, and 20 in many cases. The amplification regions on chromosomes 7, 8, 13, and 20 are shown in FIG. 2.

FIG. 13 (chromosome 7), FIG. 14 (chromosome 8), and FIG. 15 (chromosomes 13 and 20) show, in the form of a table, differences (p-values) in OS and PFS between a group having a copy number gain (CNG) and a group having no CNG in all patients (154 patients), a FOLFOX regimen group (75 patients), and a FOLFIRI regimen group (79 patients), and differences (p-values) in OS and PFS between the FOLFOX regimen group and the FOLFIRI regimen group in each of 2 groups, the group having a CNG indicated by CNG(+) and the group having no CNG indicated by CNG(−), in these chromosomal regions defined by cytobands.

A log-rank test was performed in these regions in terms of progression-free survival (PFS) and overall survival (OS) between two groups, a group of cases (patients) having amplification in the copy number of the specific region on the human chromosome and a group of cases (patients) having no amplification in all patients (154 patients). As a result, there was no significant difference in PFS in all regions. However, a significant difference was observed in OS in many regions on 7q, 13q, and chromosome 20 (see columns "OS" of columns "total (154)" in FIGS. 13, 14, and 15). Specifically, p-values in such regions were less than 0.05 (p<0.05). It is suggested that the gene amplification regions having a significant difference in OS, as described above, may include a prognostic factor.

Figure 16:
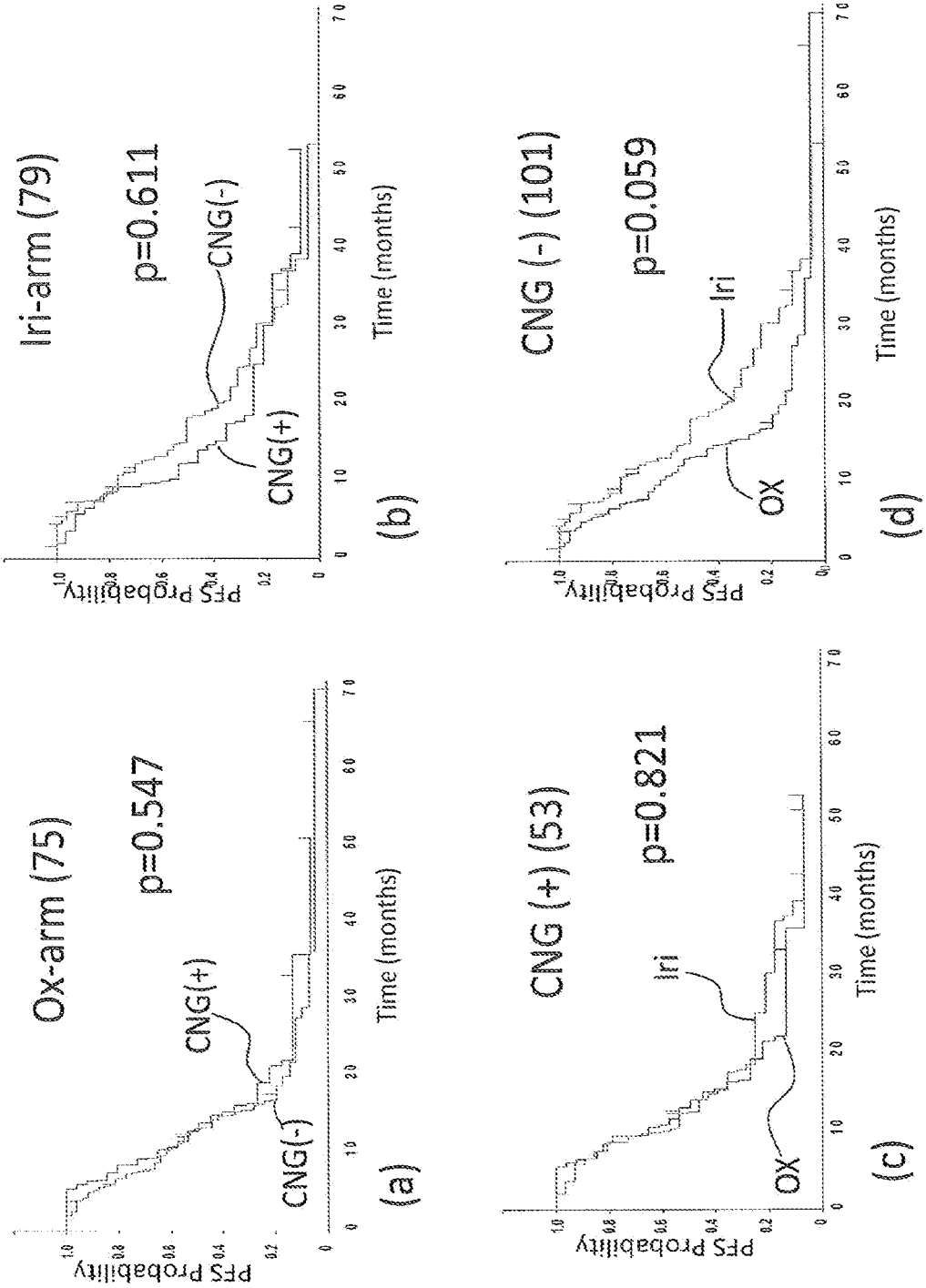
FIG. 16 is a diagram showing graphs indicating PFS plotted by Kaplan-Meier curves in a 7p15.3 region.

Referring to FIG. 13, a semi-significant difference (p<0.1) in PFS was observed in the CNG(−) group in most of the regions on a short arm 7p of chromosome 7. Among those regions, the 7p15.3 region has the smallest p-value, and Kaplan-Meier curves of PFS in this region are shown in FIG. 16.

FIG. 16(a) is a graph of the FOLFOX regimen group subdivided into the gain (CNG(+)) and no gain (CNG(−)) groups. FIG. 16(b) is a graph of the FOLFIRI regimen group subdivided into the gain (CNG(+)) and no gain (CNG(−)) groups. FIG. 16(c) is a graph of the gain (CNG(+)) group subdivided into the FOLFOX regimen and FOLFIRI regimen groups.

Further, FIG. 16(d) is a graph of the no gain (CNG(−)) group subdivided into the FOLFOX regimen and FOLFIRI regimen groups.

In all graphs, a lateral axis indicates an observation period (labelled as "Time (months)") and a longitudinal axis indicates a survival probability of PFS (labelled as "PFS Probability"). Note that, in all graphs, the lateral axes range from (month) 0 to 70 and the longitudinal axes range from 0 to 1.

Referring to FIG. 16, a semi-significant difference s having a p-value of 0.059 was observed in FIG. 16(d). That is, it is shown that the FOLFIRI regimen exhibited a higher therapeutic effect than the FOLFOX regimen in the patients having no gene amplification in this region.

Next, referring to FIG. 14, a significant difference (p=0.037) or a semi-significant difference (p=0.053) was observed in PFS in the CNG(+) group from a long arm 24.1 to 24.2 on chromosome 8 (from 8q24.1 to q24.2). Kaplan-Meier curves of OS and PFS in 8q24.1 are shown in FIG. 17 and FIG. 18, respectively.

In each figure, as in FIG. 16, a lateral axis indicates an observation period (labelled as "Time (months)") and a longitudinal axis indicates a survival probability (labelled as "OS or PFS Probability"). Further, in each figure, as in FIG. 16, (a) is a graph of the FOLFOX regimen group subdivided into the gain (CNG(+)) and no gain (CNG(−)) groups, (b) is a graph of the FOLFIRI regimen group subdivided into the gain (CNG(+)) and no gain (CNG(−)) groups, (c) is a graph of the gain (CNG(+)) group subdivided into the FOLFOX regimen group and the FOLFIRI regimen group, and (d) is a graph of the no gain (CNG(−)) group subdivided into the FOLFOX regimen group and FOLFIRI regimen group. Note that, in all graphs, the lateral axes range from (month) 0 to 70 and the longitudinal axes range from 0 to 1.

Referring to FIG. 17(a) and FIG. 17(b), OS was significantly extended in the CNG(−) group of the FOLFOX regimen group, while OS was significantly extended in the CNG(+) group of the FOLFIRI regimen group (both p-values were less than 0.05). Further, the FOLFIRI regimen group had much more favorable prognosis (p=0.004) than the FOLFOX regimen group in the CNG(+) group (see FIG. 17(c)).

Figure 17:
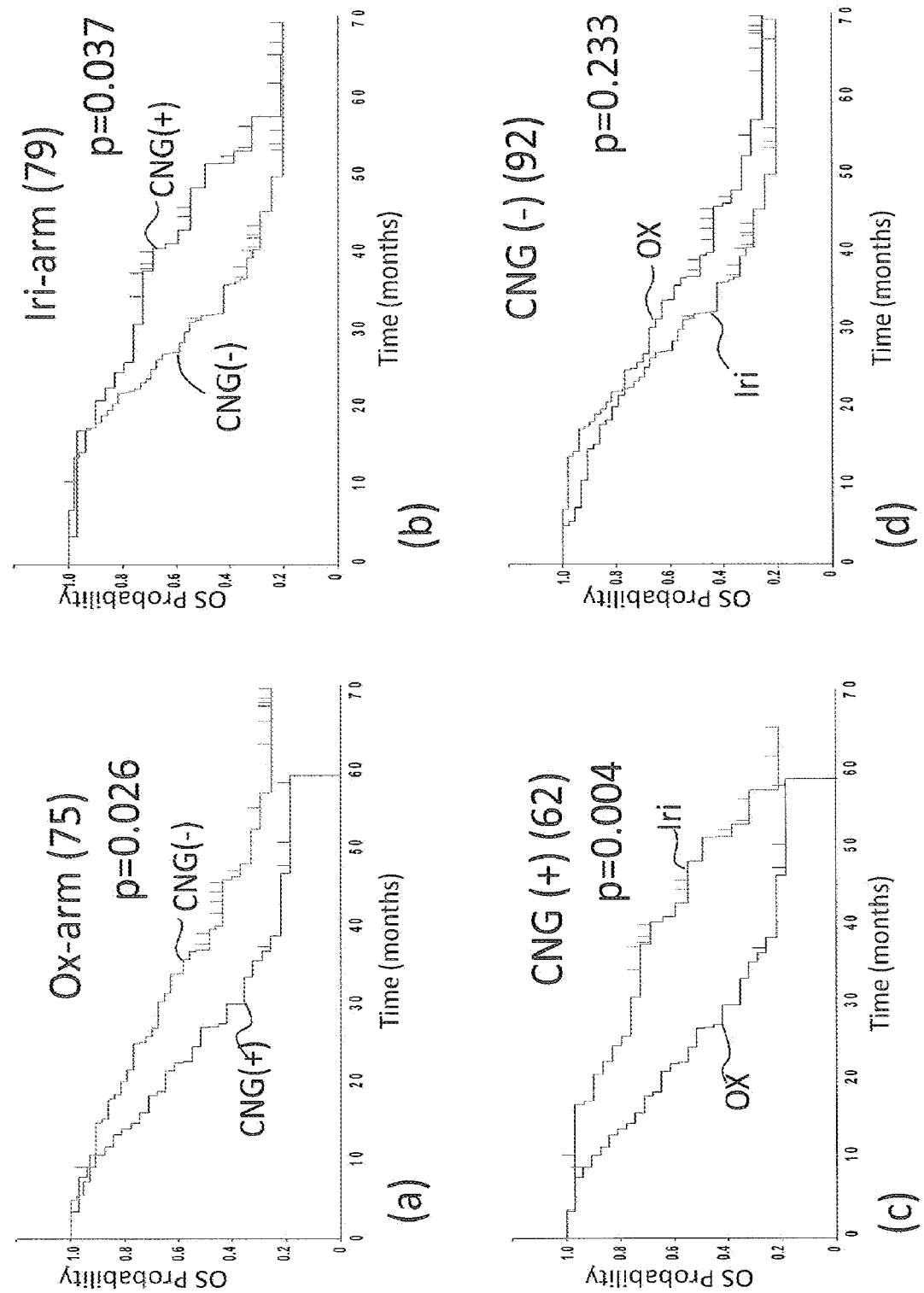
FIG. 17 is a diagram showing graphs indicating OS plotted by Kaplan-Meier curves in an 8q24.1 region.
Figure 18:
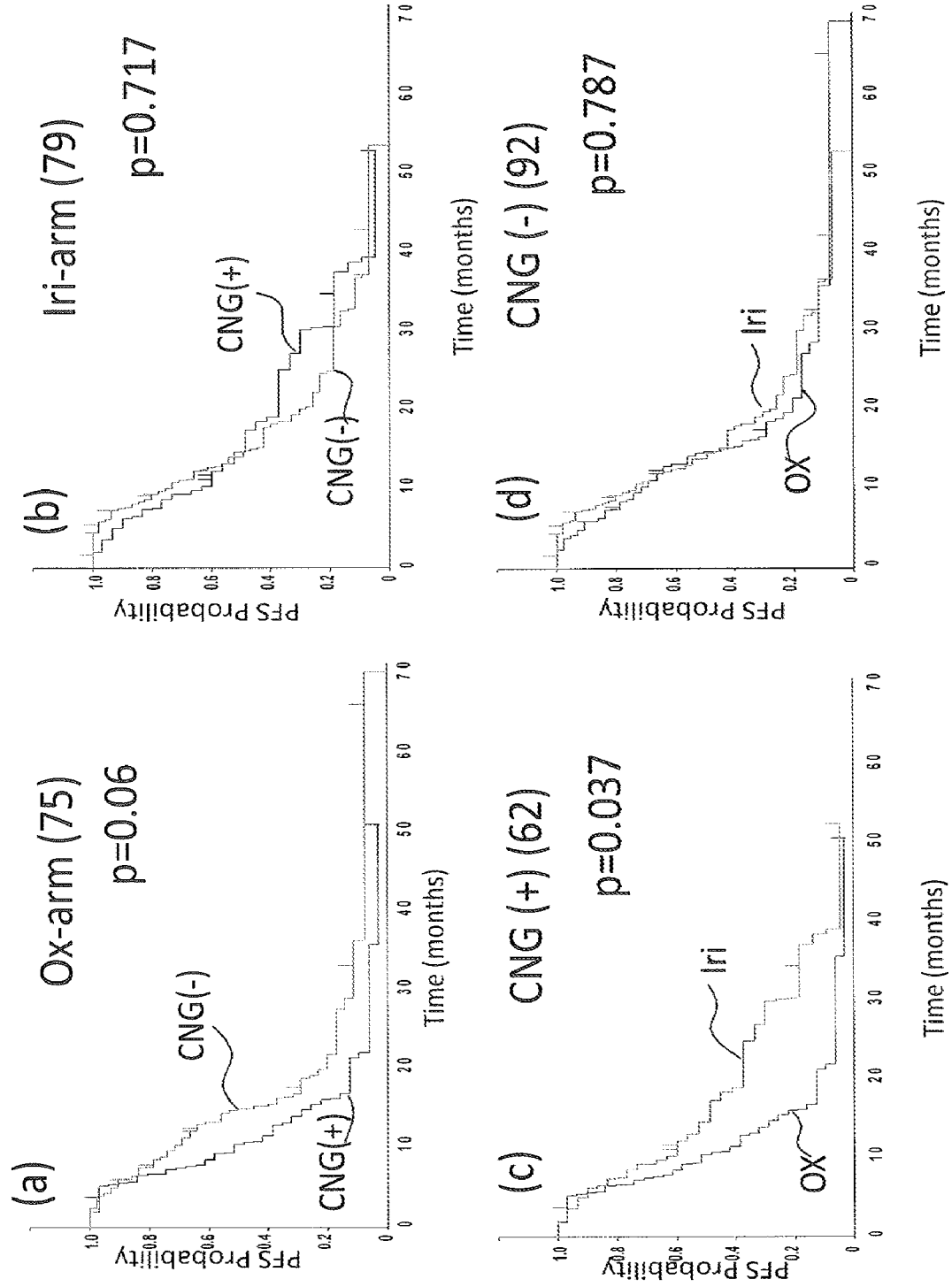
FIG. 18 is a diagram showing graphs indicating PFS plotted by Kaplan-Meier curves in an 8q24.1 region.

Referring to FIG. 18, the FOLFIRI regimen group also had a significantly higher therapeutic effect (p=0.037) than the FOLFOX regimen group in the CNG(+) group in terms of PFS (see FIG. 18(c)), which was consistent with the results in FIG. 17.

FIG. 19 and FIG. 20 show Kaplan-Meier curves of PFS and OS in 4 groups categorized on the basis of the status of CNG in 7p15.3 and 8q24.1. FIG. 19(a) and FIG. 19(b) are graphs of a group having CNG (CNG(+)) both in 7p15.3 and 8q24.1. Graphs in FIG. 19(a) and FIG. 19(b) were drawn by plotting PFS and OS, respectively.

FIG. 19(c) and FIG. 19(d) are graphs of a group having CNG (CNG(+)) in 7p15.3 and no CNG (CNG(−)) in 8q24.1. Graphs in FIG. 19(c) and FIG. 19(d) were drawn by plotting PFS and OS, respectively.

FIG. 20(a) and FIG. 20(b) are graphs of a group having no CNG (CNG(−)) in 7p15.3 and having CNG (CNG(+)) in 8q24.1. Graphs in FIG. 20(a) and FIG. 20(b) were drawn by plotting PFS and OS, respectively.

FIG. 20(c) and FIG. 20(d) are graphs of a group having no CNG (CNG(−)) both in 7p15.3 and 8q24.1. Graphs in FIG. 20(c) and FIG. 20(d) were drawn by plotting PFS and OS, respectively.

Further, in each graph, a lateral axis indicates an observation period (labelled as "Time (months)") and a longitudinal axis indicates a survival probability (labelled as "OS or PFS Probability"). Further, in each graph, the lateral axis ranges from (month) 0 to 70 and the longitudinal axis ranges from 0 to 1.

The FOLFIRI regimen group advantageously exhibited a much higher therapeutic effect in the group having CNG(−) in 7p15.3 and CNG(+) in 8q24.1 (i.e., the group of CNG (−,+): see FIGS. 20(a) and (b)).

Kaplan-Meier curves of OS (FIGS. 19(b) and (d)) showed that the FOLFIRI regimen was advantageous in the group of CNG(+,+) (FIGS. 19(a) and (b)), while the FOLFOX regimen was advantageous in the group of CNG(+,−) (FIGS. 19(c) and (d)).

That is, FIGS. 19(a) and (b) suggested that the FOLFIRI regimen was advantageous if a gain in a gene copy was observed in both regions of 7p15.3 and 8q24.1. Further, FIGS. 19(c) and (d) suggested that the FOLFOX regimen was advantageous if a gain in a gene was observed in 7p15.3 and a gain in a gene was not observed in 8q24.1.

Referring back to FIG. 14 again, in the group of cases having CNG from the 8q24.1 to 8q24.2 regions, CNG was most frequently and commonly observed (a gain in the copy numbers was observed) in the following gene group: NSMMCE2, TRBI, FAM84B, POU5F1B, LOC727677, MYC, and PVT1. These data suggested that this region may include a factor that increases an effect of the FOLFIRI regimen.

If a gene A that increases a sensitivity to the FOLFIRI (irinotecan) regimen is found, the copy number of the gene A can be measured in a patient having advanced metastatic colorectal cancer. When the copy number is gained, the combination therapy of the FOLFIRI regimen and bevacizumab can be positively selected.

Further, referring to FIG. 13, the entire 7p region including 7p15.3 may include a factor that increases an effect of the FOLFOX regimen.

FIG. 21 shows differences (p-values) in OS and PFS between a group having a gain in the copy number and a group having no gain in the copy number in all patients (154 patients), the FOLFOX regimen group (75 patients), and the FOLFIRI regimen group (79 patients) in chromosomal amplification regions other than those on chromosomes 7, 8, 13 and 20.

Figure 22:
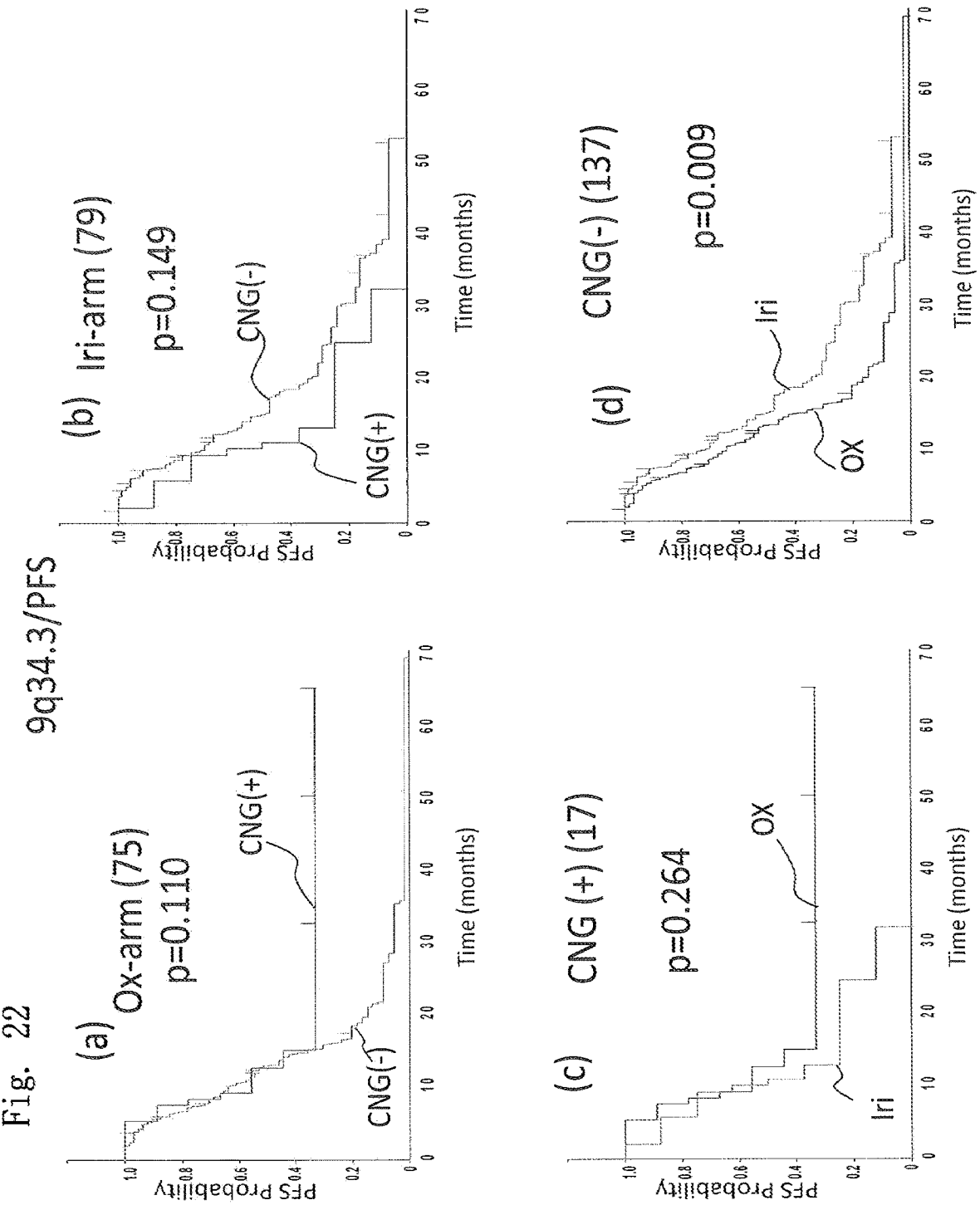
FIG. 22 is a diagram showing graphs indicating Kaplan-Meier curves in the FOLFOX group and the FOLFIRI group, each group further subdivided into the group having a copy number gain and the group having no copy number gain, and in the group having CNG indicated by CNG(+) and the group having no CNG indicated by CNG(−), each group further subdivided into the FOLFOX group and the FOLFIRI group, in an 9q34.3 region.

Among regions shown in FIG. 21, FIG. 22 shows Kaplan-Meier curves in the FOLFOX regimen group and the FOLFIRI regimen group, each group further subdivided into the group having a gain in the copy number and the group having no gain in the copy number, and Kaplan-Meier curves in the group having CNG indicated by CNG(+) and the group having no CNG indicated by CNG(−), each group further subdivided into the FOLFOX regimen group and the FOLFIRI regimen group, in the 9q34.3 region having a low p-value (0.11) particularly in terms of PFS.

FIG. 22(a) shows a graph of the FOLFOX regimen group further subdivided into the group having CNG (CNG(+)) and the group having no CNG (CNG(−)).

FIG. 22(b) shows a graph of the FOLFIRI regimen group further subdivided into the group having CNG (CNG(+)) and the group having no CNG (CNG(−)). FIG. 22(c) shows a graph of the group having CNG (CNG(+)) further subdivided into the FOLFOX regimen group and the FOLFIRI regimen group. Further, FIG. 22(d) shows a graph of the group having no CNG (CNG(−)) further subdivided into the FOLFOX regimen group and the FOLFIRI regimen group.

In all graphs, a lateral axis indicates an observation period (labelled as "Time (months)") and a longitudinal axis indicates a survival probability of PFS (labelled as "PFS Probability"). Further, in each graph, the lateral axis ranges from (month) 0 to 70 and the longitudinal axis ranges from 0 to 1.

Referring to FIG. 22(d), the FOLFIRI regimen exhibited a significantly favorable therapeutic effect in 137 cases having no gain in the copy number in this region among the total of 154 cases.

In the patients having CNG in the 9q34.3 region, CNG was most frequently and commonly observed in the following gene group: NOTCH1, EGFL7, MIR126, AGPAT2, FAM69B, and SNHG7. The genes may include a factor that increases a therapeutic effect of the FOLFOX regimen or decreases a therapeutic effect of the FOLFIRI regimen.

If such a factor B is found, the copy number of the gene B can be measured in a patient having advanced metastatic colorectal cancer. When the copy number of the gene B is not gained in the patient, the FOLFIRI (irinotecan) regimen can be preferentially selected as a combination therapy with bevacizumab. Needless to say, it is still possible to preferentially select FOLFIRI (irinotecan regimen) as a combination therapy with bevacizumab, provided that there is no CNG in the 9q34.3 region, without identifying such a gene B.

The above discussion has led to the conclusion that the genes included in 2 amplification regions of 8q24.1-q24.2 and 9q34.3 can be mentioned as a biomarker candidate that differentiates effects of 2 combination therapies and that the combination therapies can be selected by examining whether the copy numbers of 2 amplification regions of 8q24.1-q24.2 and 9q34.3 are gained.

More specifically, the FOLFIRI regimen is preferably selected in combination with bevacizumab if gene amplification is observed in the amplification region of 8q24.1-q24.2. Note that the amplification in the 8q24.1-q24.2 region includes a case where a gain in the copy number of gene is observed only in the 8q24.1 region or the 8q24.2 region. Further, the FOLFIRI regimen is preferably selected in combination with bevacizumab if gene amplification is not observed in the 9q34.3 amplification region.

INDUSTRIAL APPLICABILITY

A biomarker according to the present invention can be preferably used for determining which, a FOLFOX regimen or a FOLFIRI regimen, is selected as a treatment method of colorectal cancer.

The invention claimed is:

1. A selection method of regimens, for selecting between either a FOLFOX regimen or a FOLFIRI regimen for treating colorectal cancer, the method comprising:
   measuring a gain in a copy number of a specific region on a human chromosome in a tumor tissue specimen of the colorectal cancer, wherein the specific region on the human chromosome is at least one region among 7p15.3, 7q34, 8q24.1, 8q24.2, 8q24.1-q24.2, 9q34.3, 13q12.2, 13q14.11, 13q22.1, 13q32.2-q32.3, and 13q34; and
   selecting the FOLFIRI regimen and treating the patient having colorectal cancer with the FOLFIRI regimen when the copy number of at least one region among 7q34, 8q24.1, 8q24.2, 8q24.1-q24.2, 13q12.2, 13q14.11, 13q22.1, 13q32.2-q32.3, 13q34, 20q12, 20q13.13, 20q13.2, and 20q13.3 is gained; or selecting the FOLFIRI regimen and treating the patient having colorectal cancer with the FOLFIRI regimen when the copy number of the 9q34.3 region is not gained; or selecting the FOLFIRI regimen and treating the patient having colorectal cancer with the FOLFIRI regimen when the copy number of the 7p15.3 region is not gained; or selecting the FOLFOX regimen and treating the patient having colorectal cancer with the FOLFOX regimen when the copy number of the 7p15.3 region is gained and the copy number of the 8q24.1 region is not gained.

2. A selection method of regimens, for selecting between either a FOLFOX regimen or a FOLFIRI regimen for treating colorectal cancer in a patient, the method comprising:

measuring a gain in a copy number of a specific region on a human chromosome in a tumor tissue specimen of the colorectal cancer, wherein the specific region on the human chromosome is at least one region among 7q34, 8q24.1, 8q24.2, 8q24.1-q24.2, 13q12.2, and 13q14.11;

selecting the FOLFIRI regimen when the copy number of the specific region is gained; and treating the patient having colorectal cancer with the FOLFIRI regimen.

3. A selection method of regimens, for selecting between either a FOLFOX regimen or a FOLFIRI regimen for treating colorectal cancer in a patient, the method comprising:

measuring no gain in a copy number of a 9q34.3 region on a human chromosome in a tumor tissue specimen of the colorectal cancer;

selecting the FOLFIRI regimen when the copy number of the 9q34.3 region is not gained; and treating the patient having colorectal cancer with the FOLFIRI regimen.

4. A selection method of regimens, for selecting between either a FOLFOX regimen or a FOLFIRI regimen for treating colorectal cancer in a patient, the method comprising:

measuring a gain in a copy number of a 7p15.3 region and no gain in a copy number of a 8q24.1 region on a human chromosome in a tumor tissue specimen of the colorectal cancer;

selecting the FOLFOX regimen when the copy number of the 7p15.3 region is gained and the copy number of the 8q24.1 region is not gained; and treating the patient having colorectal cancer with the FOLFOX regimen.

\* \* \* \* \*